United States Patent [19]

Sellers

[11] Patent Number: 5,228,450
[45] Date of Patent: Jul. 20, 1993

[54] METHODS AND APPARATUS FOR AMBULATORY PHYSIOLOGICAL MONITORING

[75] Inventor: Craig S. Sellers, Red Creek, N.Y.
[73] Assignee: Diagnostic Medical Instruments, Inc., Syracuse, N.Y.
[21] Appl. No.: 695,600
[22] Filed: May 3, 1991
[51] Int. Cl.$^5$ .......................................... A61B 5/0432
[52] U.S. Cl. ................................................. 128/711
[58] Field of Search .............. 128/689, 696, 702, 710, 128/711, 712, 715, 419 PT; 364/413.06, 413.02, 413.03

[56] References Cited

U.S. PATENT DOCUMENTS

| | | | |
|---|---|---|---|
| Re. 29,921 | 2/1979 | Cherry et al. | 364/900 |
| 2,986,606 | 5/1961 | Kruse et al. | 128/715 |
| 3,221,334 | 11/1965 | Jones, Jr. | 128/717 |
| 3,897,774 | 8/1975 | Burdick et al. | 128/419 PT |
| 3,908,640 | 9/1975 | Page | 128/689 |
| 4,073,011 | 2/1978 | Cherry et al. | 364/900 |
| 4,106,495 | 8/1978 | Kennedy | 128/2.06 |
| 4,123,785 | 10/1978 | Cherry et al. | 360/6 |
| 4,136,690 | 1/1979 | Anderson et al. | 128/2.06 |
| 4,211,238 | 7/1980 | Shu et al. | 128/700 |
| 4,249,538 | 2/1981 | Musha et al. | 364/413.06 |
| 4,250,888 | 2/1981 | Grosskopf | 128/702 |
| 4,291,703 | 9/1981 | Kelen | 128/711 |
| 4,336,810 | 6/1982 | Anderson et al. | 128/702 |
| 4,400,745 | 8/1983 | Shu | 360/73 |
| 4,483,347 | 11/1984 | Wong | 128/712 |
| 4,519,398 | 5/1985 | Lisiecki et al. | 128/710 |
| 4,528,988 | 7/1985 | Wong | 128/712 |
| 4,532,934 | 8/1985 | Kelen | 128/697 |
| 4,773,097 | 9/1988 | Suzaki et al. | 364/413.02 |
| 4,883,065 | 11/1989 | Kelen | 128/711 |
| 5,058,597 | 10/1991 | Onoda et al. | 128/696 |
| 5,086,778 | 2/1992 | Mueller et al. | 128/696 |
| 5,092,341 | 3/1992 | Kelen | 128/702 |

FOREIGN PATENT DOCUMENTS

2816494 10/1979 Fed. Rep. of Germany.

OTHER PUBLICATIONS

IBM Tech. Discl. Bull., vol. 26, No. 11, Apr. 1984, pp. 6013–6015.
Loring et al., "Out-patient 24-hour Holter Monitoring: Clinical, Technical and Economic Considerations" *J. of Ambulatory Monitoring*, vol. 1, No. 1 (1988) 7–16.
Berbari et al., "An Introduction to High Resolution ECG Recordings of Cardiac Late Potentials", *Arch. Intern. Med.*, vol. 148, (Sug. 1988) 1859–1863.
Kauffmann et al., "A Study of Non-Stationary Phenomena of HRV During 24–Hour ECG Ambulatory Monitoring", *Proc. IEEE Conf. of Computers and Cardiology*, (1989) 303–306.
Smith et al., "An ECG Compression Algorithm For Full Disclosure in a Solid State Real-Time Holter Monitor", *Proc. of IEEE Conf. on Computers and Cardiology*, (1989) 569–572.
Narramore et al., "Optimising Solid State Holter Systems", *Proc. of IEEE Conf. on Computers & Cardiology*, (1989), 575–578.
Lamberti et al., "ECG Data Compression for Ambulatory Device", *Proc. of IEEE Conf. on Computers and Cardiology*, (1989), 171–174.
Sheffield et al., "Recommendations for Standards of Instrumentation and Practice in the Use of Ambulatory Electrocardiography", *Circulation*, vol. 71, No. 3, Mar. 1985.
Shah et al., "MEDICOMPACT: An ECG Data Compactor," *Proc. of IEEE Conf. on Computers and Cardiology*, (1989) 573.

*Primary Examiner*—William E. Kamm
*Attorney, Agent, or Firm*—Wolf, Greenfield & Sacks

[57] ABSTRACT

An ambulatory physiological monitor includes an input for receiving physiological data such as electrocardiography (ECG) data from a patient. This data is transferred to a disk drive by a processor or other suitable hardware. The disk drive records this data on the disk recording medium. The data is stored in noncompressed form. Preferably, to conserve power in the monitor, a buffer is also provided. The buffer temporarily holds the incoming data until the buffer is full. When the buffer is full, the disk drive is activated, and the contents are forwarded to the disk drive for storage on the disk recording medium. The monitor is switched from a low resolution mode to a high resolution mode in response to activation of an event button or at predetermined intervals.

23 Claims, 19 Drawing Sheets

METHODS AND APPARATUS FOR AMBULATORY PHYSIOLOGICAL MONITORING

FIELD OF THE INVENTION

This invention relates generally to patient monitoring systems and, more particularly, to ambulatory electrocardiography (ECG) monitors.

DESCRIPTION OF THE PRIOR ART

Monitoring of ECG data has become a useful tool in monitoring the health of a patient's heart. A prominent type of ECG monitoring is Holter monitoring in which ECG data is acquired continuously over a 24 hour period. Data acquired by Holter monitoring is useful in identifying patients who are at risk of ventricular tachycadia. To date, it has been difficult to properly identify late potentials in the data acquired by Holter monitoring. Late potentials are low level electrical signals that cause late activation of the heart within its cycle. Such late potentials can cause premature contraction and, eventually, severe fibrillation. Such late potentials have been difficult to detect because they are of too low a level (i.e., approximately 5 microvolts) and too high a frequency (i.e., approximately 250 hertz) for detection by conventional Holter monitoring systems.

Conventional ambulatory ECG Holter monitoring systems have generally fallen into two categories: solid state systems and tape based systems. Both types of systems are referred to as ambulatory systems because they are worn by a patient outside the hospital during the patient's normal daily routine. The tape based systems are provided with a magnetic tape recorder that records ECG signals acquired from electrodes that are attached at specific locations on the patient. When the 24 hour period has expired, the tape is removed from the monitor unit and the ECG signals stored therein are analyzed.

Such tape based systems suffer three primary drawbacks. First, they have a limited frequency response. This limitation stems primarily from the limited speed of operation of the tapes which limits the frequency band of ECG signals stored on the tape in a given time frame. The tapes have to move slowly so as to ensure that there is sufficient tape to record the ECG signals for the entire 24 hour monitoring. The tape units typically move at a rate in the range of one millimeter per second. Moreover, the highest frequency response is limited by the small record zone size on the tape, which also limits the frequency band of ECG signals stored on the tape. In general, such systems can operate, at best, up to a maximum frequency of 40 hertz. A second problem suffered with such tape based systems is tape motion error problems. These errors include speed changes that distort the data and recording head tracking errors. Another problem suffered by tape based systems is that it is hard to encode the occurrence of important events with precision on the tapes. For example, when a patient suffers an abnormality in his heart beat during the recording session, it is difficult to precisely encode when that event occurred with a tape based system. The resolution of such tape based systems typically is on the order of one tenth of a second. This low resolution can cause particular problems in accurately recording high frequency events such as pulses from pacemakers.

Solid state units generally utilize a memory such as a RAM built into the monitor unit. Solid state systems must rely on data compression in order to hold all of the data generated during a recording session. Typically, they have a memory capacity of 2 to 4 megabytes. Such solid state units suffer two major drawbacks. First, such memories are typically volatile so that data held in the memory is lost upon an interruption of power. A second difficulty with such solid state units concerns loss of data due to the compression. As a high level of compression is generally required to store the large amount of data acquired over the 24 monitoring hour period, the compression necessarily involves a high degree of data loss.

It is, therefore, an object of the present invention to provide an ambulatory ECG monitor with sufficient dynamic range and frequency response to accurately record late potentials.

It is a further object of the present invention to provide an ambulatory ECG monitor which employs a non-volatile memory for storing of ECG data.

It is yet another object of the present invention to provide an ambulatory ECG monitor which stores uncompressed ECG data.

It is still another object of the present invention to provide an ambulatory ECG monitor which does not suffer from motion error and positioning errors of tape recorders.

SUMMARY OF THE INVENTION

The foregoing objects are realized by an ambulatory physiological monitor for recording physiological data from a patient. The monitor includes a set of electrodes or other means for obtaining such physiological data, like ECG data. The monitor further includes a disk drive for storing the physiological data which is transferred to the disk drive by a means such as a processor. This monitor preferably includes a buffer for holding the obtained physiological data. The use of the buffer minimizes the time which the disk drive must be active and, thus, conserves the power resources of the monitor.

The physiological data is generally obtained in analog form. As such, another feature that may be incorporated into the monitor unit is a sampler for sampling the analog data to produce digital samples. The samples may be taken at many different rates including a rate greater than or equal to 200 samples per second or even a rate greater than approximately 800 samples per second. The higher sampling rate (i.e., greater than 800 samples per second) is useful for obtaining a high resolution view of the data. When ECG data is being obtained, the high resolution is helpful in locating late potentials. Also helpful in locating late potentials is for the monitor to have a wide dynamic range. Preferably, the monitor has a dynamic range of approximately 60 to 70 decibels.

When the monitor is used to obtain and record ECG information, it preferably includes a means for detecting pacemaker pulses in the ECG information. The appropriate circuitry for detecting the pacemaker pulses includes a bandpass filter for removing bands of information in which the pacemaker pulses are not likely to be found. The circuitry additionally includes a level detector for detecting the level of the ECG information. This circuitry may be provided with appropriate means for indicating on the disk recording medium that a pacemaker pulse has been detected by the circuitry.

The monitor is preferably independently powered by a self-contained power supply. This power supply may comprise at least one battery. As mentioned above, if the monitor is powered by a self-contained power source, it is desirable to conserve its power usage. One means for conserving the power usage is to only transfer data to the disk drive when the buffer for holding the data is substantially full. The data is preferably stored on the disk recording means in non-compressed form so that no data is lost.

Additional components that may be incorporated into the monitor include an interface for interfacing the monitor with a data processing system. Through this interface, the data processing system may read data stored on the disk recording medium. The monitor may also include a display for displaying information such as status and error messages to a user of the monitor. A suitable display is a liquid crystal display (LCD). Furthermore, the monitor may be provided with a means wherein the patient may mark the occurrence of an important event on the disk recording medium.

DETAILED DESCRIPTION OF A PREFERRED EMBODIMENT

Figure 1:
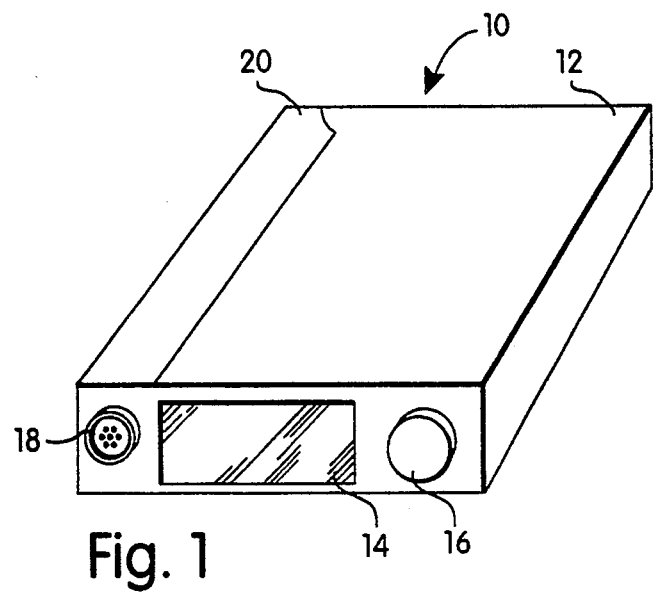
FIG. 1 is a perspective view of the ambulatory ECG monitor unit.

In accordance with a preferred embodiment of the present invention, an ambulatory ECG system includes a monitor recording unit 10 such as shown in FIG. 1 for recording ECG data from a patient. The monitor unit 10 is encased within a durable housing 12 made of plastic or other durable material which can withstand reasonable shock, temperatures and compression. The monitor unit 10 is of an appropriate size and shape so that it may be readily carried by the patient. The illustrative embodiment of FIG. 1 is polyhedral in shape and has dimensions of 1.3 inches in height, 3.6 inches in width and 5.1 inches in depth. The entire unit 10 only weighs 15 ounces. It should be appreciated that the shape, weight, and the dimensions shown in FIG. 1 are purely illustrative. Those skilled in the art will know of other suitable shapes and dimensions. Preferably, monitor unit 10 is of an appropriate size and shape so that it may be conveniently worn on a patient's belt with a suitable attachment such as a holster 11 shown in FIG. 3.

Located on the front face of the monitor unit 10 is a display 14 for displaying status messages and the time of day. The display 14 may be a conventional liquid crystal display (LCD). Also located on the front face of the monitor unit 10 is an event button 16. This button allows the patient to record the time an event such as the suffering of chest pains occurred so that the ECG data recorded at that time can be flagged for closer examination. Lastly, the front face of the monitor unit 10 includes a seven pin connector 18 for connecting electrodes that gather ECG signals with the monitor unit 10.

Figure 2A:
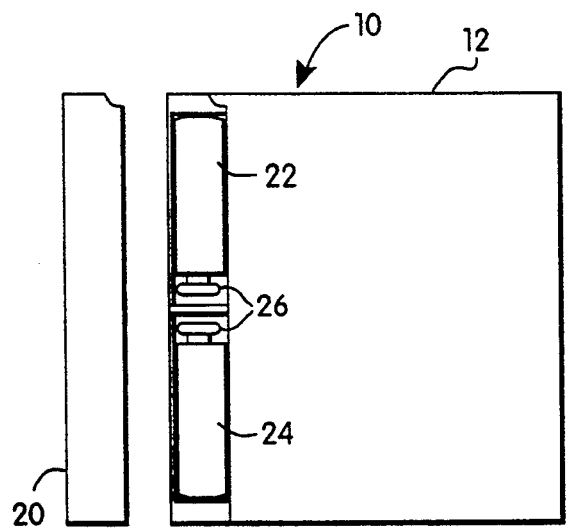
FIG. 2A is a top view of the ambulatory ECG monitor unit of FIG. 1.

As shown in FIG. 2A, the monitor unit 10 is powered by two conventional 9 volt radio batteries 22 and 24 which fit into the housing 12 underneath a sliding battery door 20. These batteries serve as a power supply to energize the monitor unit 10. The invention is not limited to use of such 9 volt batteries; rather battery configurations, such as configurations employing AA batteries, may similarly be used. Batteries 22 and 24 are connected to the internal components of the unit via electrical connectors 26.

Figure 2B:
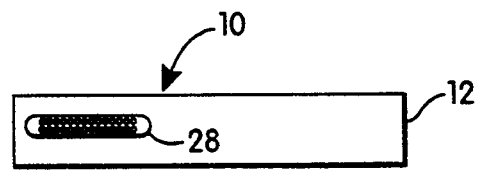
FIG. 2B is a rear view of the ambulatory ECG monitor unit of FIG. 1.

As shown in FIG. 2B, the rear face of the monitor 10 incorporates a pin connector 28 for connecting the monitor unit 10 to an external system such as a data processing system. This connection allows data recorded by the monitor unit 10 to be retrieved by such an external system and facilitates communications between the external system and the monitor unit. Data retrieved via the connector 28 may be processed by such an external system using well known algorithms for analyzing ECG data. Processing hardware, however, may also be directly incorporated within the monitor unit.

Figure 3:
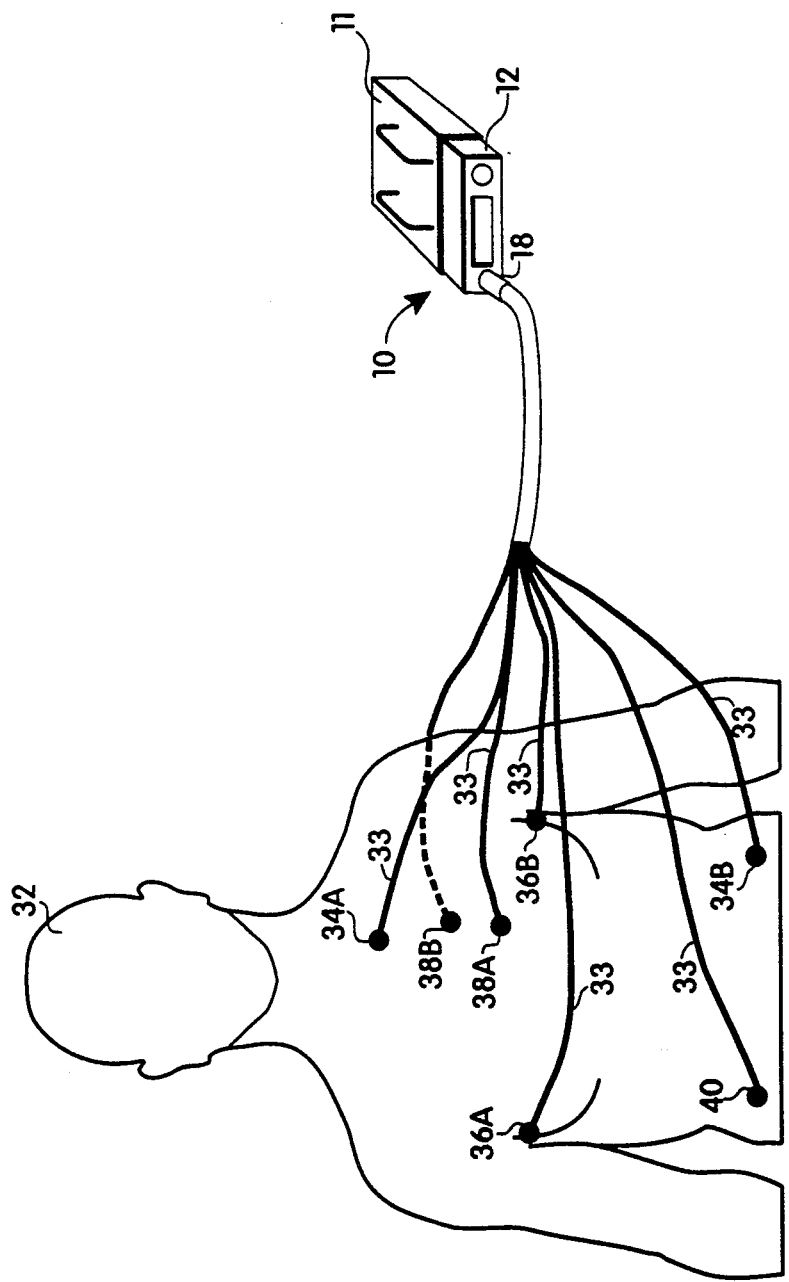
FIG. 3 diagrammically illustrates typical electrode placements and the connection of the electrodes to the ambulatory ECG monitor unit.

The monitor unit 10 is designed for use with a set of electrodes. In most applications, either two or three sets of electrodes are employed. For illustrative purposes, the discussion that follows will focus on the use of three sets of electrodes. In particular, as depicted in FIG. 3. three sets of electrodes 34a, 34b, 36a, 36b, 38a and 38b are employed to provide a three dimensional view of heart activity. The three pairs of electrodes provide ECG signals from the X, Y and Z axes of the patient, respectively. Note that the lead wire 33 for electrode 38b is shown in phantom because the electrode is placed on the patient's back (i.e., it is displaced relative to electrode 38a in the Z direction). This pattern of electrode placement corresponds to a standard established by the Association for the Advancement of Medical Instrumentation (AAMI). Also employed is a reference or ground electrode 40.

The electrodes may be conventional are pre-gelled ECG silver chloride electrodes. These electrodes operate in pairs (i.e., 34a works as a pair with 34b, etc.) so that the three sets of electrodes 34a, 34b, 36 a, 36b, 38a and 38b provide three channels of analog ECG input. Each electrode is provided with a lead wire 33 that leads to the pin connector 18. As shown in FIG. 1, connector 18 has seven pins, that is one pin for each electrode.

ECG signals retrieved from the electrodes are processed and stored by hardware located inside the monitor unit 10. This hardware includes a 2½ inch disk drive 40 (see FIG. 4) such as a Prairie 242 disk drive sold by PrairieTek Corporation. The hardware additionally includes a printed circuit board containing components which will be described in more detail below. The disk drive 40 and the printed circuit board are connected to the external pin connector 28 through a driver circuit 58.

Figure 4:
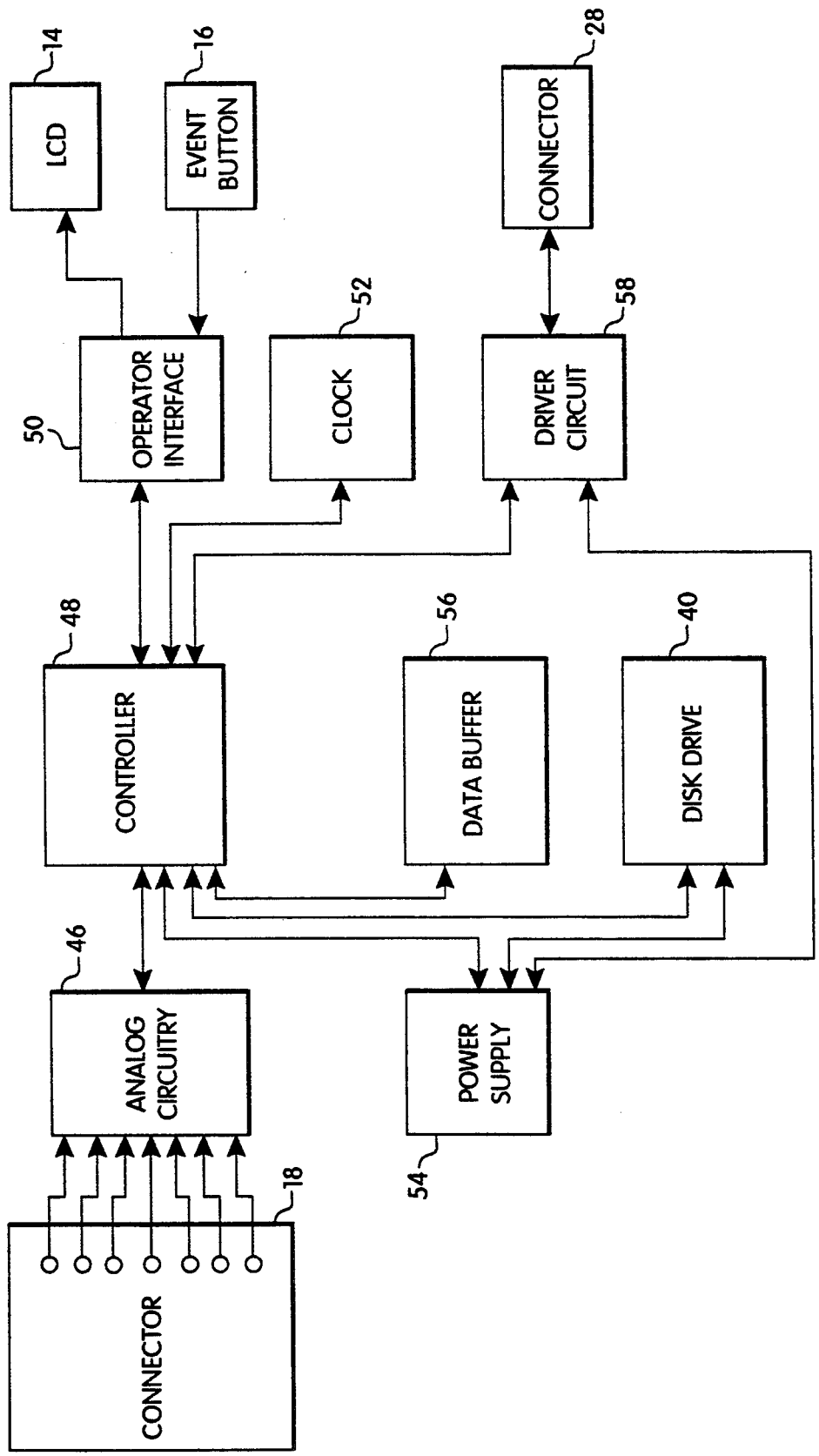
FIG. 4 is a block diagram depicting the major components of the ambulatory ECG monitor unit of FIG. 1.

FIG. 4 diagrammically illustrates the major components of the monitor unit 10 in block form. The monitor unit 10 includes electrode connector 18 as previously described. This connector 18 is coupled to analog circuitry 46 that amplifies and processes the input ECG signals received through connector 18. The analog circuitry 46 is connected to a controller 48 that controls the operation of the monitor and converts amplified analog ECG signals into digital form. The controller 48 is connected to a power supply 54, which, as described above, may constitute two conventional 9 volt batteries 22 and 24 (see FIG. 2a). The controller 48 is also coupled to the disk drive 40 which is used to store the digital ECG data. The disk drive 40, like the controller 48, is powered by the power supply 54. In addition, the controller 48 is coupled to a data buffer 56 which temporarily holds the digital ECG data before this data is written to disk by the disk drive 40.

The internal components of the monitor unit 10 also include an operator interface 50 which is connected to the display 14 and the event button 16. Still further, the monitor is provided with a real time clock 52. The real time clock 52 has a non-volatile memory which is used to hold system status information. This memory is provided with its own battery to protect the data held therein in the event that main monitor power is interrupted.

Figure 5:
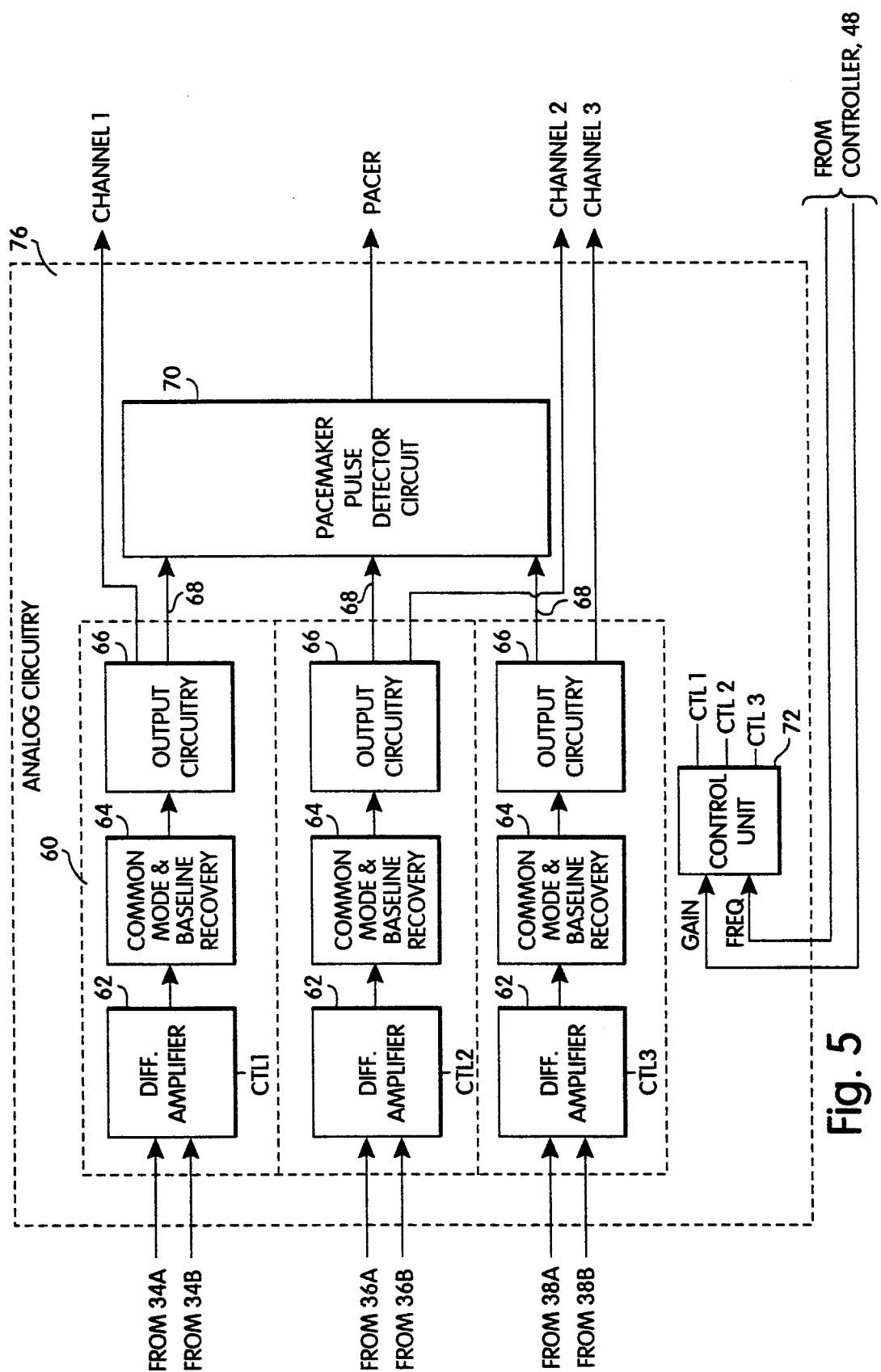
FIG. 5 is a more detailed block diagram illustrating the components of the analog circuitry shown in FIG. 4.

FIG. 5 depicts the analog circuitry 46 of FIG. 4 in more detail. The analog circuitry 46 contains separate sets of like circuitry 60 that operate on input from a respective pair of electrodes 34a, 34b, 36a, 36b, 38a and 38b. Hence, when three pairs of electrodes are used, the analog circuitry 46 includes three sets of circuitry 60. Each such set of circuitry includes a differential amplifier circuit 62 employing amplifiers such as the Motorola MC34184D. The differential amplifier circuit 62 receives the inputs from a respective pair of electrodes and generates an output corresponding to the difference between the levels of the two signals.

The gain and frequency response of each of the differential amplifier circuits 62 is dictated by a respective set of control signals which are denoted as CTL1, CTL2 and CTL3 in FIG. 5. These control signals originate from a control unit 72 that receives gain and frequency information from the controller 48. The use of such control signals and differential amplifier circuits is well known in the prior art and will not be discussed in detail herein.

The output from each differential amplifier circuit 62 passes to a conventional common mode and base line recovery circuit 64. Suitable amplifiers for this circuit include Motorola MC34184D amplifiers. The output from each common mode and base line recovery circuit 64 passes to output circuitry 66. The output circuitry 66 forwards the output (which constitutes a respective channel of data) to the controller 48. As seen in FIG. 5, a separate output circuit 66 provided for the channel 1, channel 2 and channel 3 outputs. Each common mode and base line recovery circuits 64 also forwards the output to a pacemaker pulse detection circuit 70 which analyses the signal to determine if it includes a pacemaker pulse.

The ability to identify the presence of a pacemaker pulse and the time it occurs is greatly helpful to medical personnel who are examining a patient. In particular, it allows the determination of the time delay between a stimulus (i.e. a pacemaker pulse) and a heart beat. Further, such monitoring can help to determine whether a pacemaker is malfunctioning.

Figure 6:
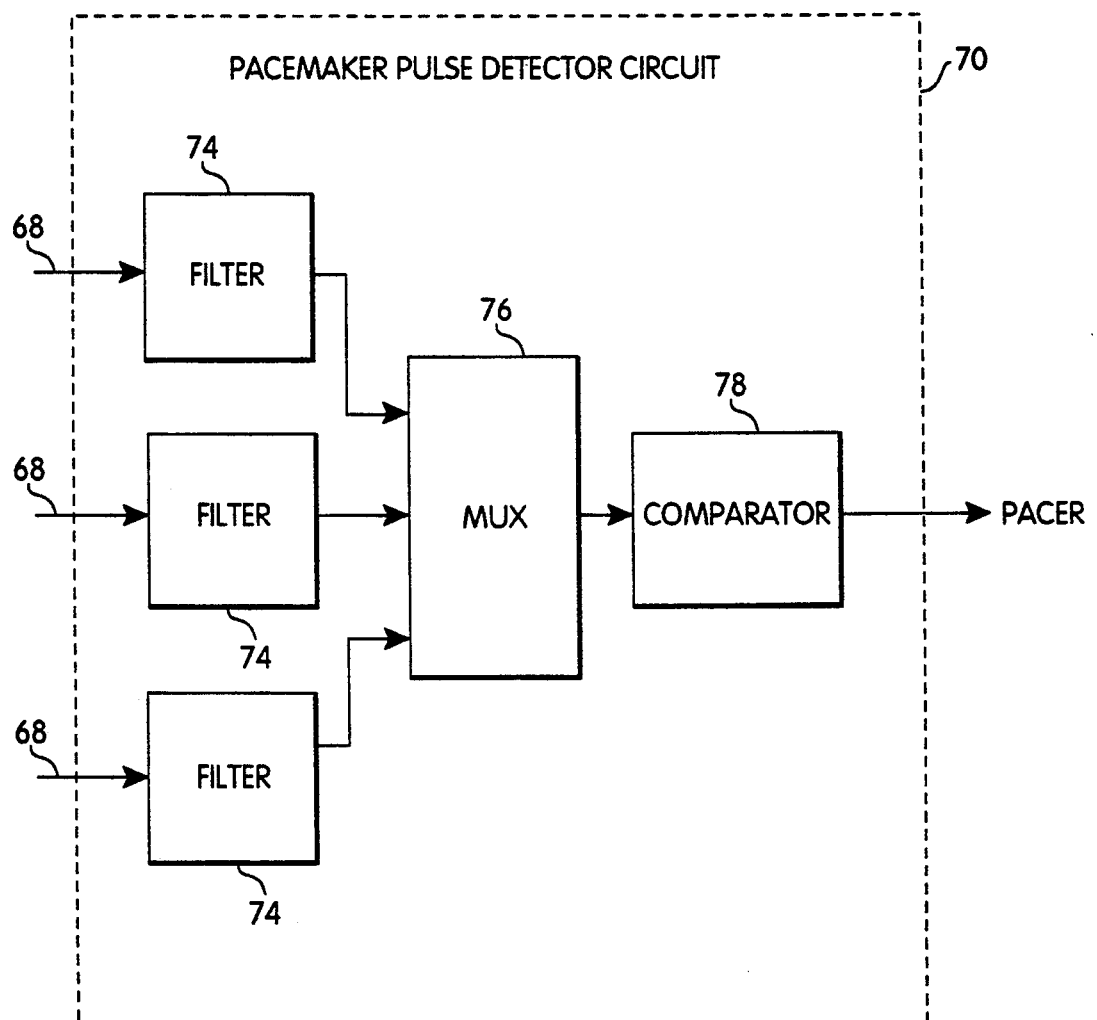
FIG. 6 is a more detailed block diagram illustrating the components of the pace pulse detector circuit of FIG. 4.

FIG. 6 depicts the pacemaker pulse detector circuit 70 in more detail. This circuit interrupts the controller 48 with an output denoted as "Pacer" when a pacemaker pulse is detected. In particular, this circuit 70 determines whether the amplitude of each of the received signals exceeds a given threshold level; hence indicating that the signal is likely a pacemaker pulse. The pacemaker pulse detector circuit 70 includes a filter 74 for each input 68. The filters 74 are bandpass filters that pass signals in the range of approximately 40 to 100 hertz. These filters may be implemented using amplifiers such as the Maxim ICL761DCSE and other conventional components. This filter eliminates those sections of the frequency range in which pacemaker pulses are not likely to be detected. The filtered outputs are then compared by a comparator circuit 78 that compares the filtered outputs with an amplitude threshold The threshold is programmably selectable so that appropriate threshold may be selected for a particular patient. The circuit includes a multiplexer 76 such as a Maxim DG212CSE which selects the filter output be compared by the comparator circuit 78. Due to the use of the multiplexer, one or more channels may be selectively monitored for the presence of such pacemaker pulses. The result of the comparison by the comparator circuit 78 is passed to the controller as the "Pacer" signal. The "Pacer" signal interrupts the controller 48 when a pace pulse is detected.

Figure 7:
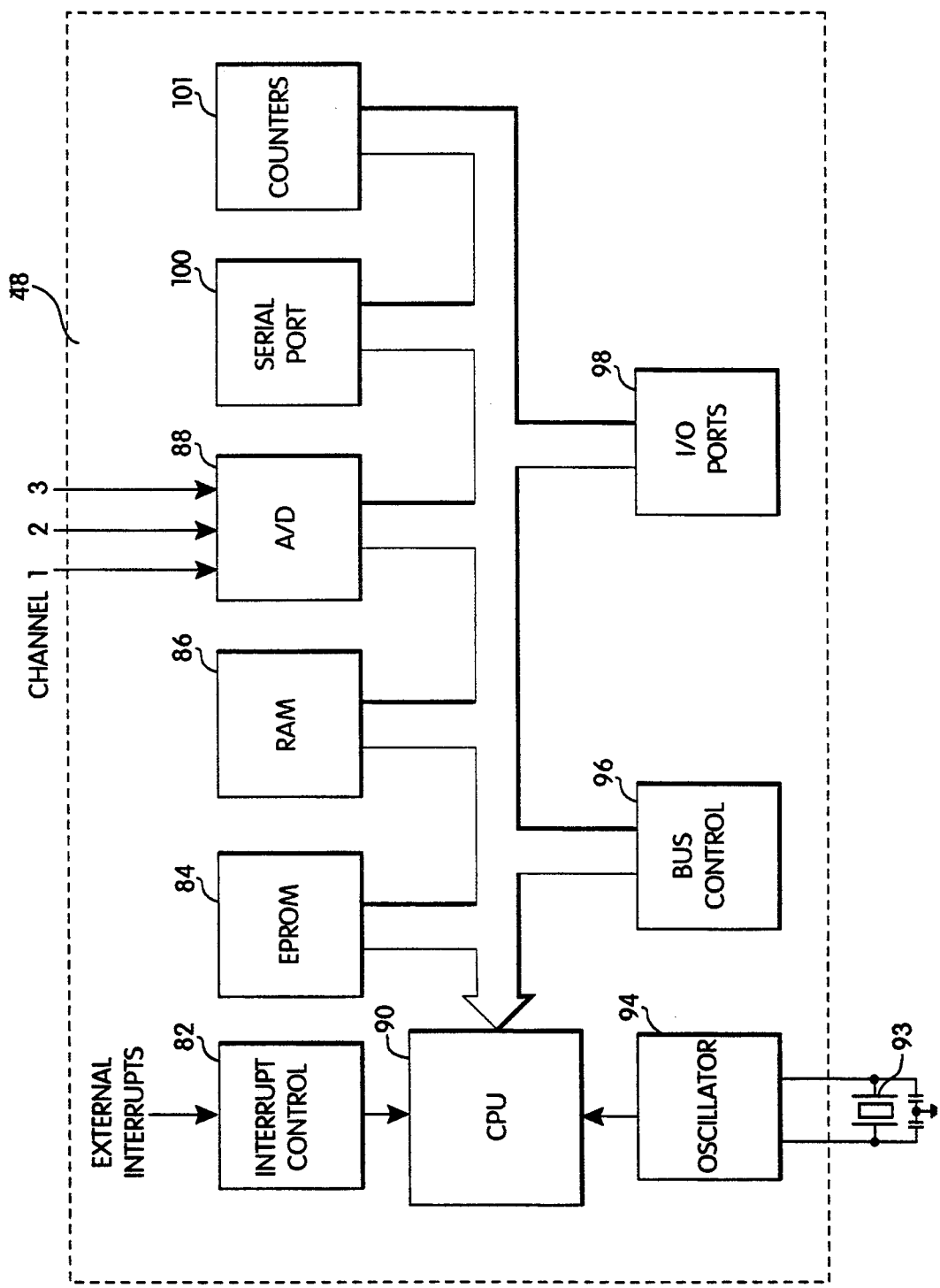
FIG. 7 is a more detailed block diagram illustrating, the components of the controller of FIG. 4.

FIG. 7 diagrammically illustrates the components of the controller 48 in more detail. The controller 48 is provided with two separate memories, an EPROM 84 and a RAM 86. The EPROM 84 holds approximately 8 kilobytes of memory, whereas the RAM 86 holds 256 bytes of memory. The EPROM 84 is used to store instructions to be executed by the CPU 90. The RAM is used as a buffer for incoming ECG data and for other special types of data including pacer and event data.

The controller 48 further includes a CPU 90 for controlling operation of the monitor unit 10. The CPU 90, the EPROM 84 and the RAM 86 are all individually coupled to an internal bus 92 which facilitates communication between components connected thereto. To handle interrupts, the controller 48 has an interrupt controller 82. The controller, includes an oscillator 94 with an external crystal 93 which is connected to the CPU 90. The internal oscillator may operate at 12 megahertz wherein each system clock cycle is comprised of twelve oscillator cycles (i.e., 1 microsecond). The controller additionally includes three counters 101 that are used for system timing. The third timer is a watchdog timer that is used to reset the microcontroller if the controller enters an erroneous processor state.

Also coupled to the internal bus 92 of the controller 48 is a bus controller 96 The bus controller 96 regulates access to the internal bus 92. An additional component connected to the internal bus 92 is an analog to digital converter (ADC) 88. ADC 88 produces 10 bit digital samples from the analog channels 1, 2 and 3. The ADC 88 includes a buffer for temporarily holding the digital samples it produces. All 10 bits are used when the system is operating in a high resolution mode. The eight highest order bits are used when the system operates in a lower resolution mode. These two modes of operation will be discussed in more detail below. The internal bus is also connected to input/output (I/0) ports 98 and a serial port 100. A suitable controller incorporating all of these components is the Signetics 87C552 sold by the Signetics Company. Nevertheless, other controllers can be used.

Figure 8:
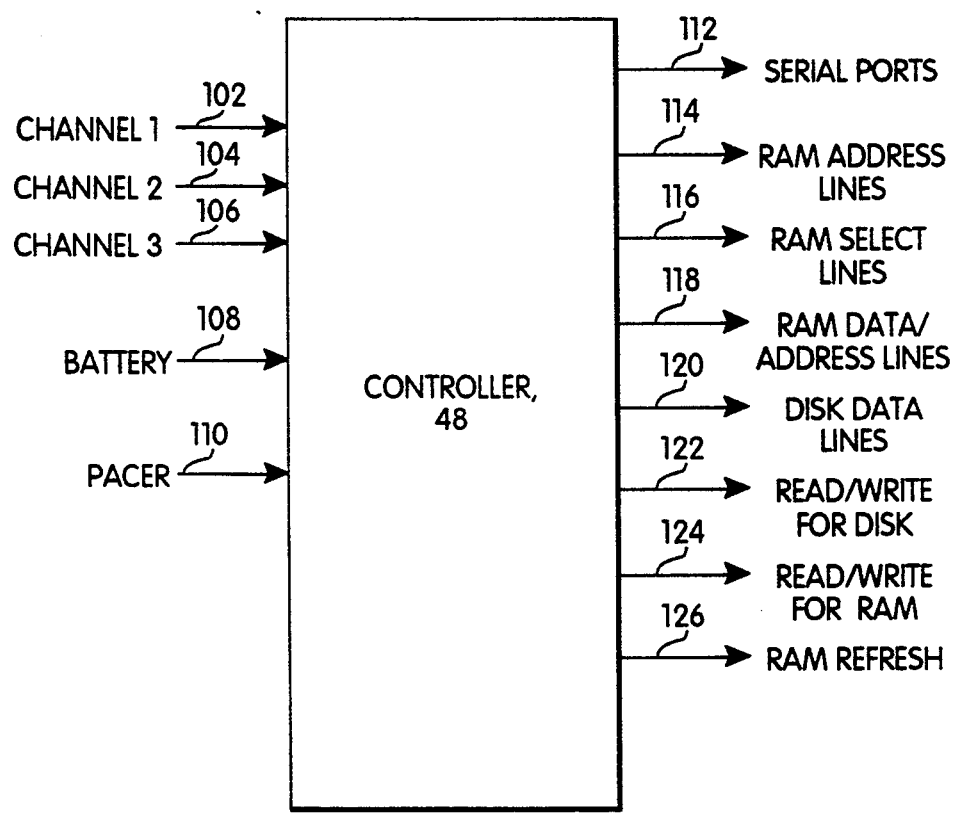
FIG. 8 is a block diagram illustrating the inputs and outputs of the controller of FIG. 4.

FIG. 8 illustrates the pin configuration of the controller 48. The controller receives analog ECG signals as input over channels 1, 2 and 3 from the analog circuitry through sets of pins 102, 104, 106. As mentioned previously, signals in these three channels are converted into digital samples by the internal ADC 88 of the controller 48 (see FIG. 7). The controller 48 also receives, status information through pins 108 regarding the status of the batteries or power supply. If the batteries are too low, this status information is used to prompt a message on the LCD, warning the user of the drained batteries. Also, the controller 48 receives the "Pacer" interrupt through pin 110 when a pacemaker pulse is detected by the analog circuitry 46.

The controller 48 also has a number of pins used to carry output signals. In particular, it includes a serial port 112. Likewise, it has a number of address lines for sending addresses to the data buffer 56 (see FIG. 4). Furthermore, the controller includes a number of data pins 118 that may be used to transmit either data or addresses to the data buffer. As will be explained below in more detail, in the preferred embodiment, two RAMs 130 and 132 (see FIG. 9) are employed in the data buffer 56. As a result, when communicating with the data buffer 56, the controller 48 must indicate which RAM is selected. To accomplish such a selection, the controller has pins that are connected to RAM select lines. Only the selected RAM will be active at any time. Also provided at the controller 48 are read/write lines 124 which carry read or write pulses to the RAMs from the controller and a RAM refresh line 126 for refreshing the pseudo static RAMs of the data buffer.

The controller 48 further includes lines for carrying signals to the disk drive 40 (see FIG. 4). In particular, the controller 48 has a number of output pins 120 that are used for carrying data to the disk drive 40. It is over these lines that the digital samples of ECG data are forwarded for storage in the buffer and on the disk. Further, a pin 122 is provided for connection to lines that carry read and write pulses to the disk drive.

Figure 9:
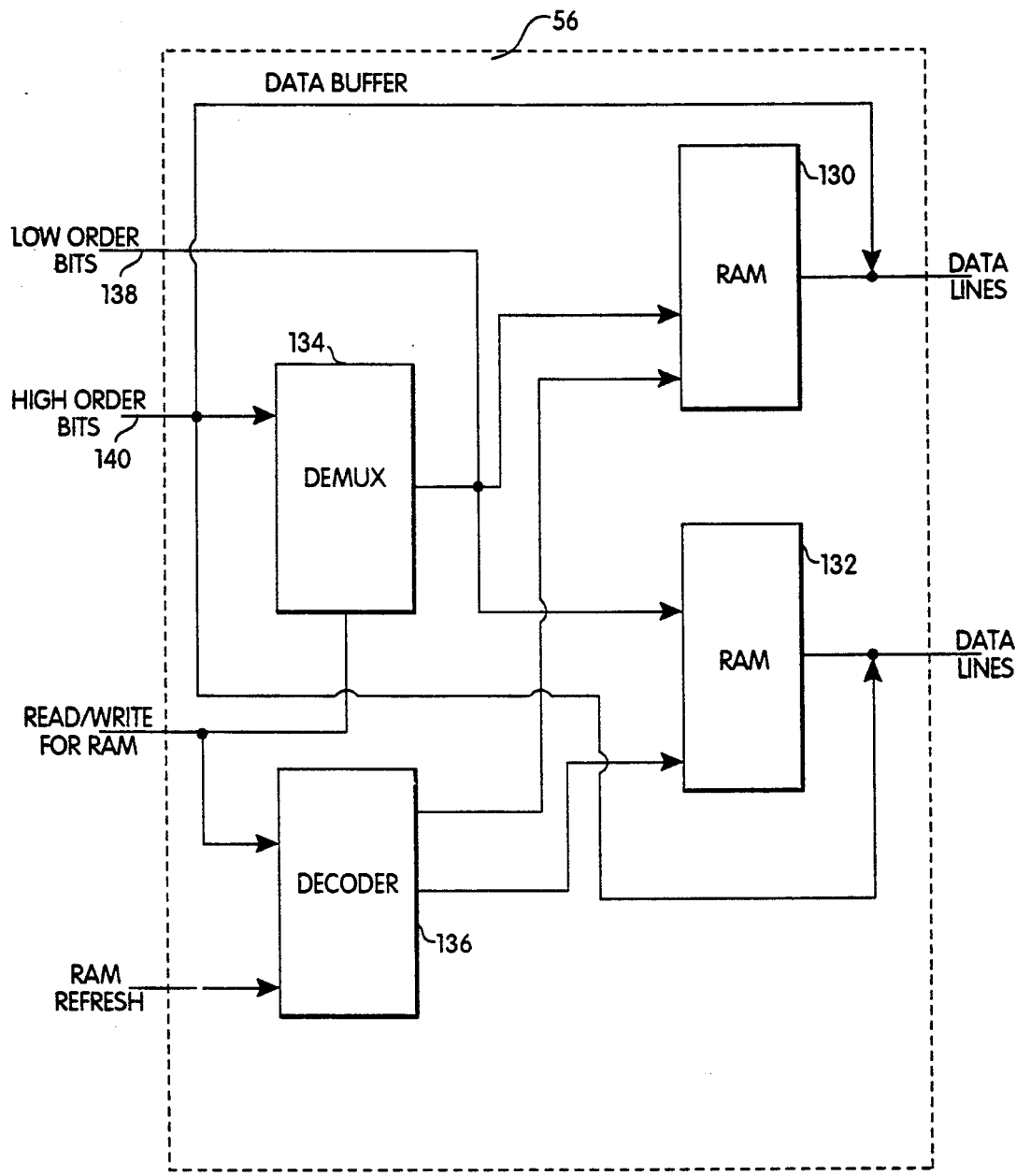
FIG. 9 is a more detailed block diagram depicting the components of the data buffer of FIG. 4.

The data buffer 56 is shown in more detail in FIG. 9. Specifically, the data buffer 56 includes two pseudo static RAMs, 130 and 132. Suitable RAMs are Hitachi HM 658512 pseudo static RAMs. Other RAMs may, likewise, be used. Each of these RAMs holds 524,288 bytes of memory. In the present case, each of these RAMs are divided into three buffers: a data buffer, an event buffer and a pacer buffer. Separate read and write pointers are maintained for each of the three buffers. The data buffer 56 also includes a demultiplexer 134 and a decoder 136.

The function of the demultiplexer 134 is best understood by looking at the data and address outputs of the data buffer 56. As shown in FIG. 9, the low order bits for an address to access either of the RAMs 130 or 132 come from pins 138 that are exclusively dedicated to transmitting address bits. However, the high order bits for an address to access either of the RAMs 130 or 132 are output from the controller on pins that can carry both addresses and data. As a result, it is necessary to differentiate whether data or an address is being transmitted over these pins when a transfer is made. The demultiplexer 134 latches the addresses into the RAMs as the higher order bits of the address when addresses are being transmitted to the RAMs. However, if data is being transferred rather than an address, the demultiplexer does not latch the address into the RAMs. Instead, the data is passed to the data lines of the respective RAMs 130 and 132 so that the active. RAM receives the data. The select for the demultiplexer 134 is the read/write signal for the RAMs which is issued by the controller. When the signal indicates a read, the demultiplexer 134 latches the address into the respective RAMs, whereas if the signal indicates a write, the data is forwarded to the data lines.

The data buffer 56 further includes a decoder 136 for decoding the control signals forwarded from the controller to the data buffer 56. In particular, decoder 136 receives the RAM refresh signal from the controller as well as the read/write signal for the RAMs of the data buffer. It then generates appropriate signals to the respective RAMs.

To understand how the monitor unit 10 operates, it is useful to examine the flow of signals and data through the monitor unit. Initially, analog ECG signals are acquired through the electrodes 34a, 34b, 36a, 36b, 38a and 38b. The analog ECG signals travel over the lead wires 33 to the monitor unit 10 (see FIG. 3). This data passes through the seven pin connector 18 to the analog circuitry 46 as shown in FIG. 4. In the analog circuitry 46, the signals from the respective pairs of electrodes are processed in parallel by the circuitry 60 as shown in FIG. 5. The differential amplifiers 62 amplify the input signals which are passed to the common mode and base line recovery circuits 64 in accordance with the gain and frequency response that is programmed by the controller. The ECG signals are then forwarded to the output circuitry 66. The output circuitry passes the signals onto the controller 48. The pacemaker pulse detector circuit 70 examines the signals to determine whether their amplitude exceeds a given threshold, hence constituting a pacemaker pulse. Specifically, as depicted in FIG. 6, selected channel outputs pass through the bandpass filter 74 to the multiplexer 76, which selects the outputs for comparison by the comparator circuit 78. The selected output is compared by the comparator circuit 78, and the results of the comparison are passed to a buffer 80. If a pacemaker pulse is detected an interrupt is forwarded to the controller 48 (FIG. 4).

The ECG signals from the three channels pass from the analog circuitry 46 (see FIG. 4) to the controller 48. In the controller, as shown in FIG. 7, the signals pass to ADC 88. ADC 88 converts the signals into ten bit digital samples. The sampling rate of ADC 88 is controlled by the CPU 90 of the controller 48 as will be explained in more detail below. The CPU 90 forwards the digitized data to the data buffer 56 over the RAM data/address line 118 (see FIG. 8), and the data is written into one of the RAMs 130, 132 in the data buffer 56.

When one of the RAMs 130, 132 is nearly full, the CPU 90 of the controller 48 (see FIG. 7) reads out the entire contents of the respective RAM 130, 132 and forwards the contents to the disk drive 40 (see FIG. 4) wherein the data is written onto disk. The disk drive 40 is active only when a RAM is nearly full This approach conserves power by only operating the disk drive when necessary. Specifically, the use of the buffer RAMs allows the disk drive only to be active for short intervals. Generally, the disk is active for twenty seconds for every eighty minutes of monitoring. Furthermore, since the disk can store approximately 42 megabytes of data, it has sufficient memory capacity to store all of the data received over the twenty four hour monitoring period without the need for data compression. As a result, there is not a problem of data loss suffered by prior art solid state systems. The CPU 90 (see FIG. 6) is programmed such that it will only operate for twenty four hours. Once twenty four hours have elapsed, the system idles and does not accept any more ECG signals from the patient.

Figure 10:
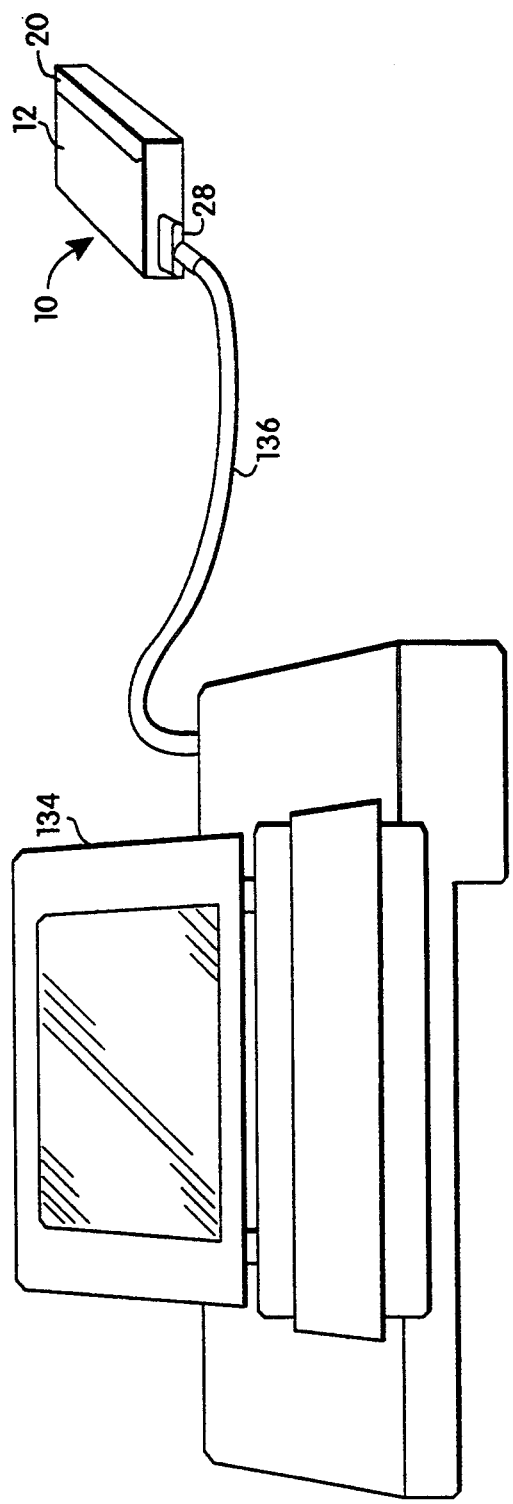
FIG. 10 diagrammically illustrates the connection of the ambulatory ECG monitor unit to a data processing system.

Once a Holter recording session is concluded, the data on the disk of the disk drive 40 (see FIG. 4) is downloaded to a computer system such as shown in FIG. 10. If the analysis processing hardware is included in the monitor unit 10, however, such downloading is not necessary. As shown in FIG. 10, a cable 136 is connected to the external connector 28 and a data processing system 134. This allows the transmission of data between the monitor unit 10 and the data processing system 134. A dedicated data bus connects the disk drive 40 to the external connector 28. This data bus is within the driver circuitry 58 connecting the disk drive 40 with the connector 28 and allows the data processing system 134 to gain direct access to the data on the disk drive 40. As a result, the controller is not involved in the data transfer. Rather, the disk drive 40 is isolated from the controller. Hence, the data processing system 134 may treat the disk drive 40 as if it were a typical peripheral device connected to the data processing system.

It should be appreciated, nevertheless, that a typical data processing system 134 such as a personal computer need not be used to download the data. Rather, a special module for interfacing with the external connector 28 may be provided to extract the data from the monitor unit 10.

When the monitoring unit is recording data, it can be operated in either a high resolution mode or a low resolution mode. In the high resolution mode, the unit 10 takes samples at a rate of 1,000 samples per second, thereby recording the ECG signals over a wide frequency band. As mentioned above, in this mode all ten bits of the samples are stored. In the low resolution mode, only 200 samples per second are taken. In this mode, only eight bits of the samples are stored. This rate of sampling in the low resolution mode is still higher than conventional systems and, thus, is better able to detect late potentials. The monitor unit 10 is also better able to detect late potentials because of its large dynamic range, which is on the order of 40 to 60 decibels.

The CPU 90 (see FIG. 7) of the controller 48 is programmed such that it initially operates in a mode specified by the non volatile memory of the clock 52. This memory holds status information that is used to recover the state of the monitor, should the monitor lose power or otherwise stop operating. The modes include the high resolution mode. The CPU 90 may be toggled into the high resolution mode in two ways. First, the software for the CPU 90 may be programmed such that when the event button 16 (see FIG. 1) is pushed, the CPU shifts the unit 10 to high resolution mode for a predetermined time period. Second, the CPU may be programmed so that at predetermined intervals it automatically enters the high resolution mode. The high resolution mode is generally active for a short duration, such as ten minutes. The duration that the system is active in the high resolution mode is programmable. Further, the system may be programmed such that when this high resolution mode is completed, the monitor unit 10 switches back to the low resolution mode. In general, when the high resolution mode is completed, the system returns to an initial state wherein it looks to the non volatile memory of the clock to determine its current mode of operation.

Figure 11:
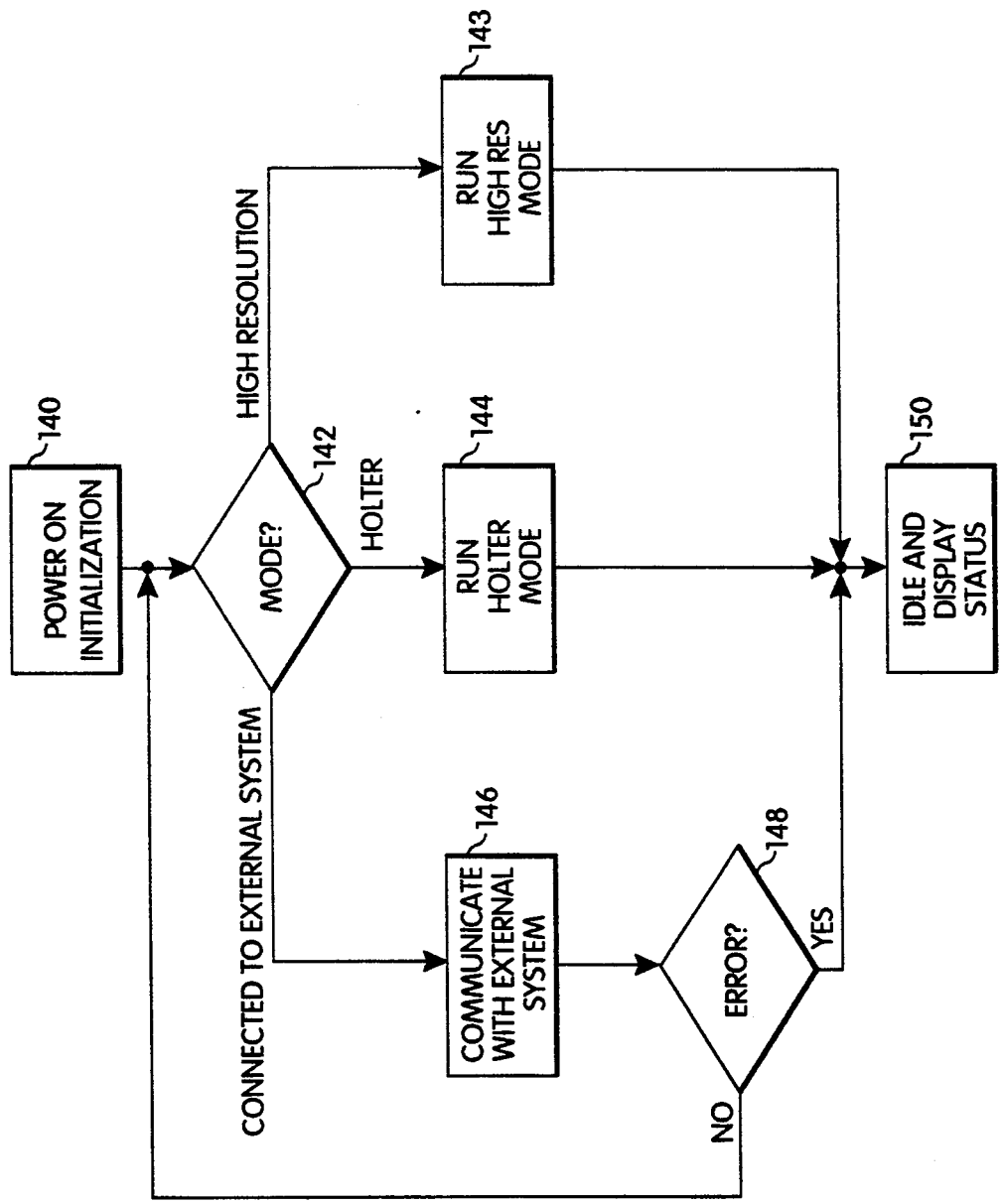
FIG. 11 is a flow chart of the basic operation of software for the CPU of FIG. 7.

FIG. 11 shows a flow chart of the basic steps performed by the CPU 90 when the monitor is powered up. In particular, on power up, the CPU 90 executes an initialization routine to prepare the monitor unit for operation (step 140). Part of the initialization routine is to examine the status information held in the non-volatile clock memory, including information regarding the current mode of operation. Upon completion of the initialization routine, the CPU determines the current mode of operation of the system (step 142). If the system is operating in high resolution mode, the controller 48 runs a high resolution mode routine (step 143). Similarly, if the system is in Holter mode, the controller 48 runs a Holter mode routine (step 144). Lastly, the system may run an external connection routine that facilitate connection of the monitor unit to an external device. When running the external connection routine, the CPU communicates with the connected external system (step 146). In addition, the CPU checks for errors (step 148). If an error has not occurred during the communication with the external system, the CPU returns to its initial state wherein it again determines its current mode of operation (step 142). However, if an error occurs, the CPU idles and prompts the display of an error message (step 150). The CPU also idles and displays a final status message upon completion of the Holter mode or the high resolution mode.

Figure 12A:
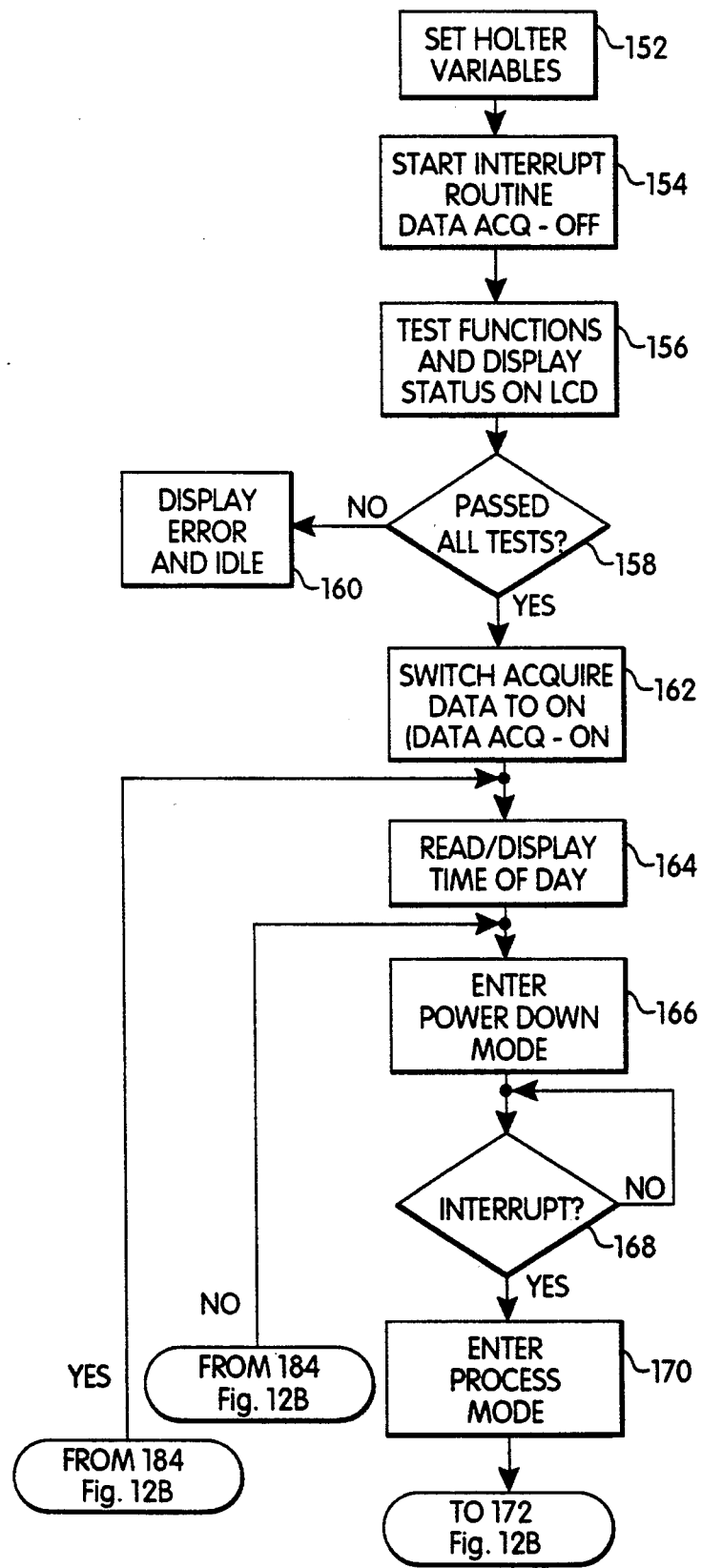
FIGS. 12A, 12B and 12C are flow charts depicting the steps of the Holter mode routine performed by the CPU of FIG. 7.
Figure 12B:
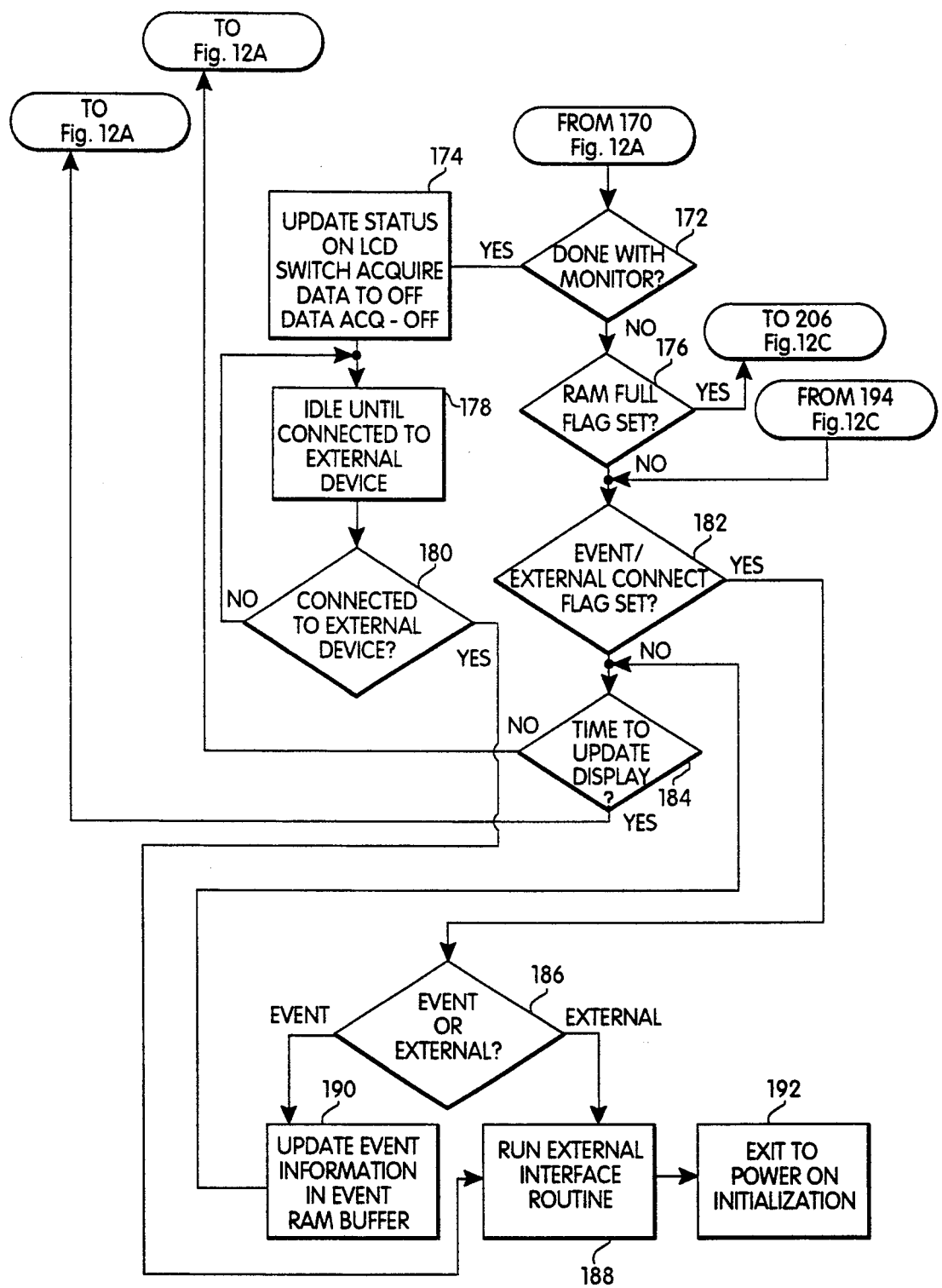

FIGS. 12A-12D are flow charts of the steps performed when the unit is operating in the Holter mode. As shown in FIGS. 12A and 12B, the CPU initially sets system variables including status flags in the non-volatile memory so that the variables are proper for operation in the Holter mode (step 152). It then initiates the interrupt routine shown in FIG. 12D but does not begin data acquisition (step 154). Next, a short test sequence is initiated and the status is displayed on the display 14 (step 156). The system subsequently checks to see whether all tests have been passed (step 158), and if a test has failed, the error is displayed on the display 14 and the processor idles (step 160).

If all the tests were successfully completed, the system enables a data acquisition mode (step 162), which will be described below. In this mode, the system determines the time of day from clock 52 (see FIG. 4) and displays this time on the display 14 (step 164 in FIG. 12A). The CPU 90 then enters power-down mode (step 166) and waits for an interrupt (see step 168). When an interrupt is received, the CPU 90 awakens and enters a process mode (step 170). In the process mode, the system determines if the monitor unit 10 has completed data acquisition (step 172), (i.e., whether time has expired). If the system has reached completion, the CPU 90 updates the status on the display and acquires no more data (step 174). The system then idles until it is connected to an external device (step 178). The system continuously tests for connection to an external device (step 180). When the monitor unit is connected to an external device, it runs the external interface routine (step 188). Upon completion of the external interface routine, the unit returns to the power up initialization step of FIG. 11 (step 192).

In the instance wherein the system is in process mode and is not done with the monitor (see step 172), it determines whether the RAMs of the data buffer are full by checking whether a RAM FULL flag as been set (step 176). If the RAM FULL flag has not been set, the system determines whether an event/external connect flag has been set (step 182). If the event/external connect flag has not been set, the system determines whether the display should be updated (step 184). If it is not time to update the display, (i.e., does the time of the clock matches the displayed time), the system returns to the power down mode (step 166). In contrast, if the display requires updating, the system reads the updated time from the clock 52 (FIG. 4) and displays the updated time on the display (step 164, FIG. 12A).

When the event/external connect flag is set at step 182, the CPU 90 determines which of the two possible events that may set this flag has occurred. If the event button triggered setting of the flag, the event data held in the event buffer section of the internal RAM 86 (see FIG. 7) is updated (step 190, FIG. 12A). Specifically, when the event button is pushed, the system records the time from clock 52 and from counters 101 in the internal RAM that is eventually forwarded to an event buffer of the RAMs 130 and 132 of the data buffer as will be described below. Next, the above-described step of determining whether it is time to update the display (i.e., step 184) is performed. If, an external connection triggered the flag, the external interface routine is run (step 188).

Figure 12C:
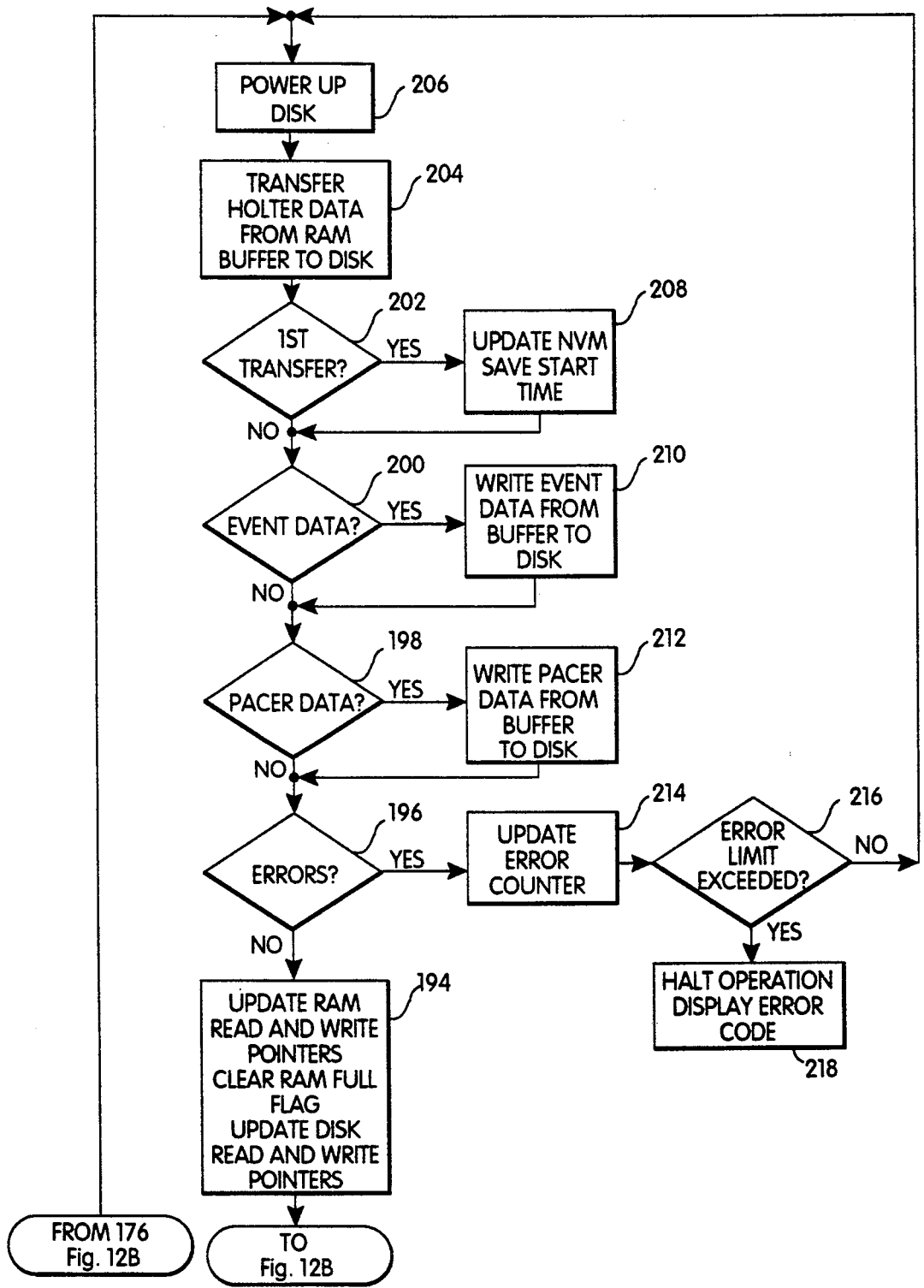

The above discussion focuses on the instance at step 176 wherein the RAM FULL flag indicates that the RAM is not full. When the RAM FULL flag is set, the steps of FIG. 12C are performed. In particular, the disk drive is powered up (step 206). Powering up the disk drive only for short intervals, as mentioned above, helps to conserve power. When the disk drive is fully powered up, the Holter ECG data is transferred from the RAM in the data buffer to the disk drive (step 204). In performing each transfer of ECG data, the system determines whether the transfer is a first transfer (step 202). In the case of a first transfer, the status information of the non-volatile memory of the clock is updated to reflect the start time of the transfer. If the data transfer is not the first transfer, the CPU determines whether event data is present in the event buffer portion of the RAM (step 200). If event data is present, the event data is written from the event data buffer portion of the RAM to the disk (step 210). The system then determines whether pacer data is present in the pacer buffer portion of the RAM (step 198). If pacer data is present, the pacer data is written from the appropriate portion of the RAM to the disk (step 212). In particular, when a pacer interrupt is sent, the system stores the time of the pacer interrupt. The pacer data referred to above is this time information. Subsequently, the system determines whether any errors have occurred (step 196). If an error has occurred, the error counter is updated (step 214). The system then determines whether a predetermined error limit has been exceeded (step 216). If the limit has not been exceeded, the system returns to transferring Holter data. If the error limit has been exceeded, the system halts operation and displays an error code (step 218). In the event that no errors have occurred, the system updates read and write pointers contained within the RAMs, clears the RAM FULL flag and, updates the disk read and write pointers (step 194). The system then returns to step 182 as depicted in FIG. 12B.

Figure 12D:
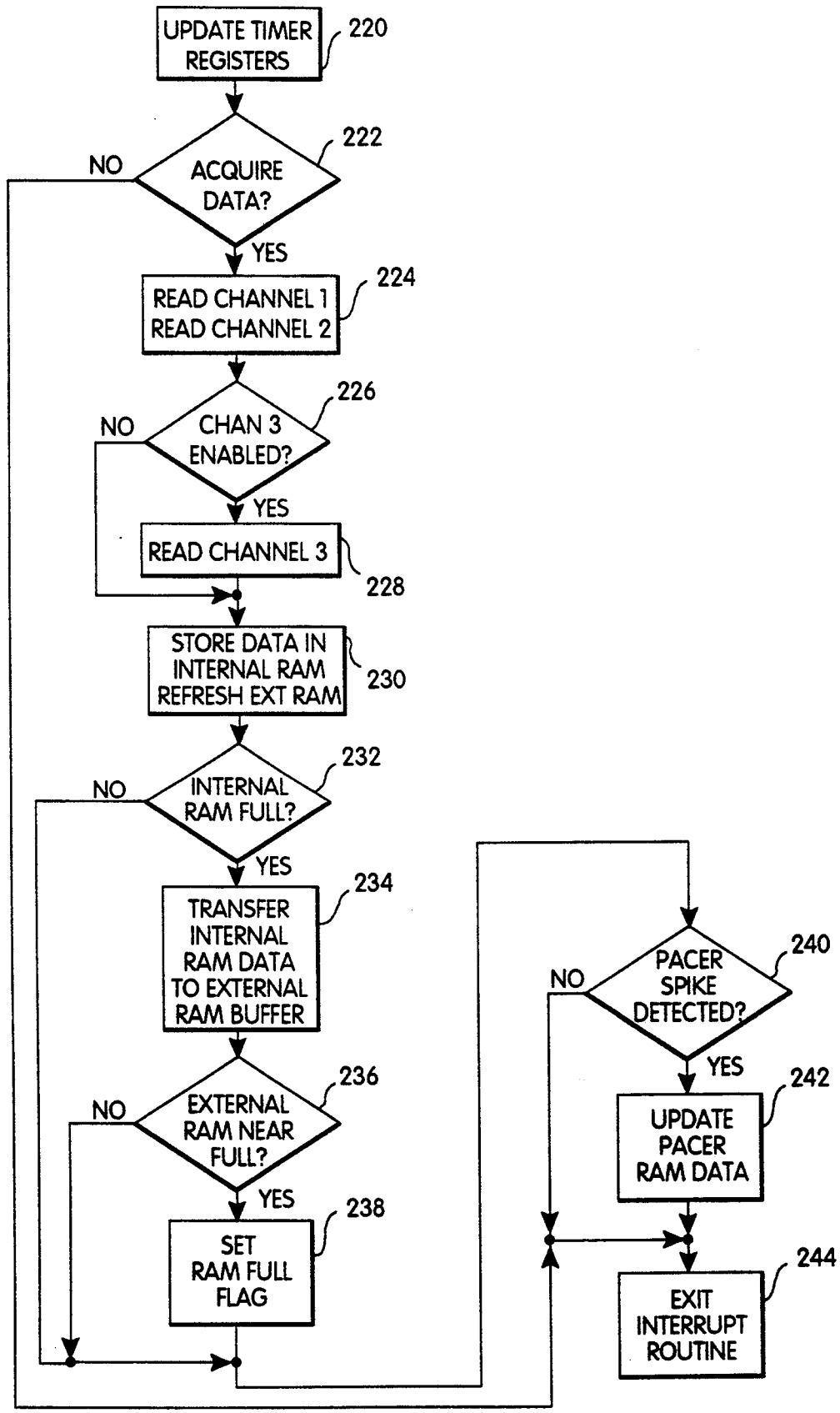
FIG. 12D is a flow chart of the interrupt routine performed by the CPU of FIG. 7 when in the Holter mode.

The interrupt routine that is called in step 154 of FIG. 12A(a is depicted as a flow chart in FIG. 12D. The interrupt routine is run in the foreground of the CPU of the controller. The remaining time slots of the CPU are filled by the routines of FIGS. 12A-12C which may be said to run in the background of the CPU. The interrupt routine serves primarily to acquire new ECG data.

In accordance with the interrupt routine, the counters 101 in the controllers are initially updated (step 220). If the system is in a mode wherein it is not acquiring data, (see step 222) the system exits the interrupt routine (step 244). If the system, however, is in a mode where it is acquiring data, (see step 222) it reads the first and second channels of data from the buffer of the ADC (step 224). The system determines whether the third channel is enabled (step 226). The monitor unit 10 may be used with either two or set three sets of electrodes. If the third channel is not enabled (step 226), the system skips the third channel. If, in contrast, the third channel is enabled, the system reads the data in the third channel (step 228).

The data read by the system is stored in the internal RAM of the controller, and the external RAMs of the data buffer are refreshed via the refresh RAM signal sent from the controller (step 230). The system next determines whether the internal RAM is full (step 232). If the internal RAM is full, the data held in the internal RAM is transferred to the external RAMs of the data buffer (step 234). The system subsequently determines whether the external RAM of the data buffer is nearly full (step 236). If the external RAM is nearly full, the RAM FULL flag is set (step 238).

When the internal RAM is not full (see step 232), if the RAM FULL flag has been set (see step 238) or the external RAM is not near full (see step 236), the system determines whether a pacemaker pulse has been detected by the pacemaker pulse detector circuit (step 240). If no pacemaker pulse has been detected, the system exits the interrupt routine. If a pacemaker pulse has been detected by the pacer detection circuit, pacemaker data held in the internal RAM is updated to include the time of the detected pulse (step 242). The controller then exits the interrupt routine (step 244).

Figure 13A:
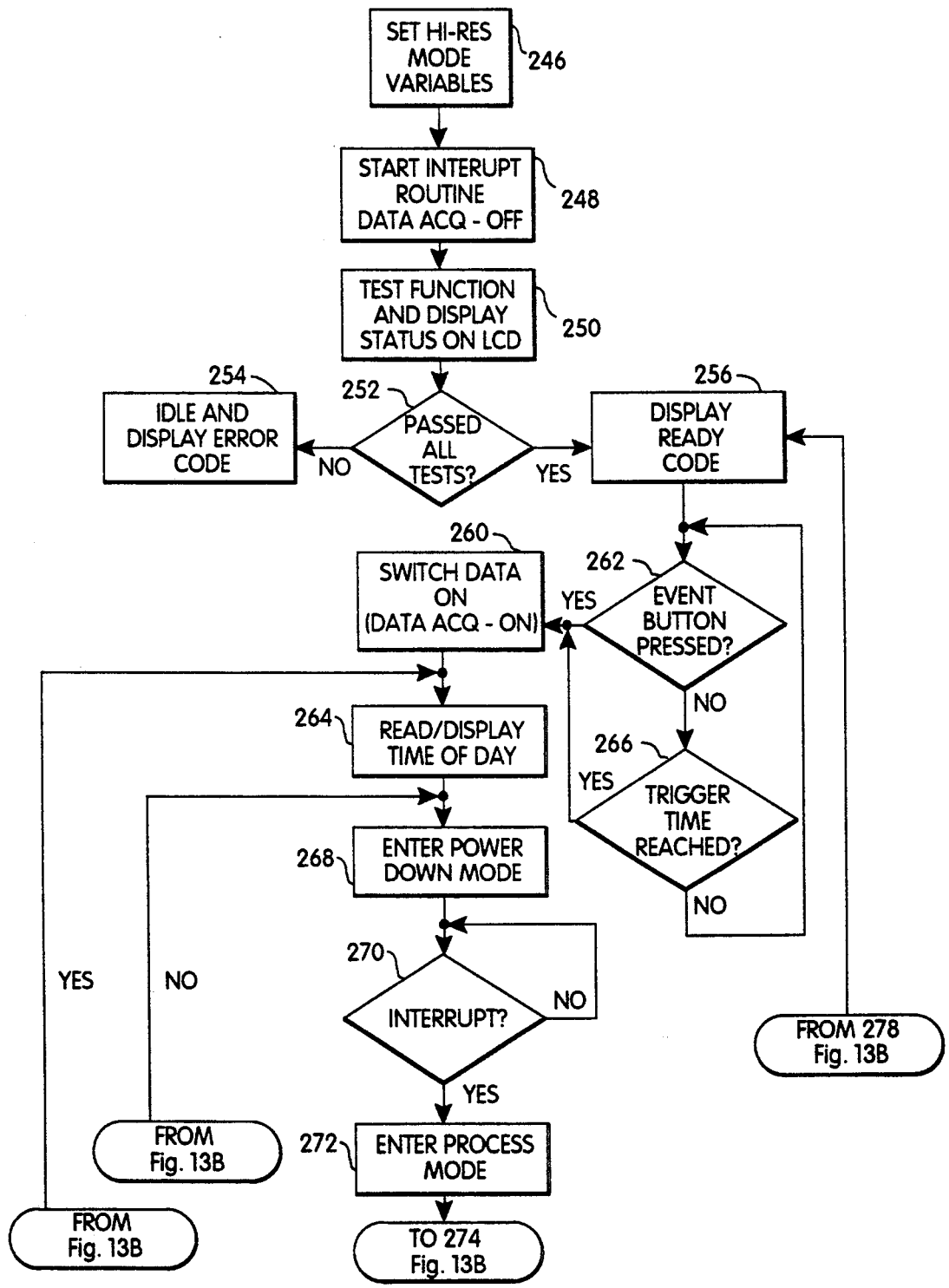
FIGS. 13A, 13B and 13C are flow charts depicting the steps performed by the CPU of FIG. 7 when operating in high resolution mode.
Figure 13B:
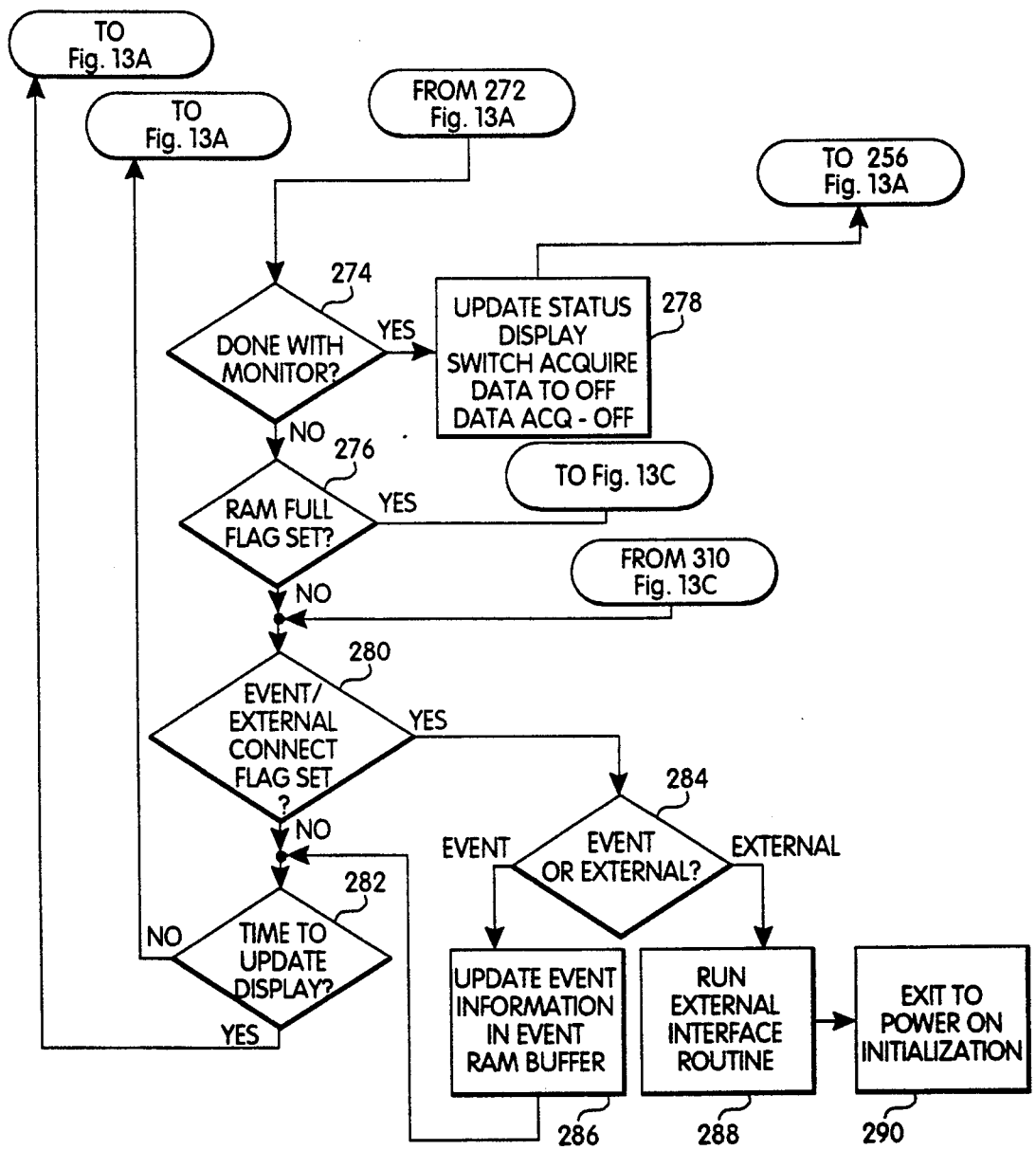

FIGS. 13A-13D show the steps performed by the system when operating in the high resolution mode. As shown in FIGS. 13A and 13B, the controller initially sets system variables for operation in the high resolution mode (step 246). The system then starts an appropriate interrupt routine but does not yet begin data acquisition (step 248). The system then tests the functions of the monitor and posts the results of the tests on the display (step 250). The system determines whether all tests have been passed (step 252) and idles if an error has occurred. When an error arises during the testing, the display exhibits an error message identifying the error (step 254). If all tests are passed, the system displays a ready code on the LCD (step 256). The system then determines whether the event button has been pressed (step 262). If the event button was not pressed, the system determines whether a software programmable trigger time has been reached (step 266). The trigger time is reached when a predetermined clock value is obtained. The system continues to check for these two events until one such event occurs. If the event button is pressed or if the trigger time is reached, the system enters a data acquisition mode (step 260). The system then reads and displays the time of day on the display (step 264).

The controller next enters a power down mode (step 268) wherein it checks continuously for an interrupt (step 270) that awakens it from the power down mode. When an interrupt occurs, the system enters a process mode similar to operation in the Holter mode (step 272). Upon entering the process mode, the system determines whether the system is done with the monitor procedure (step 274). If the system is done with the monitor procedure (i.e., no more data is to be acquired), it updates the system status on the display and stops acquiring data (step 278). The system then displays a ready code (step 256).

If the system is not done, it determines whether the RAM FULL flag has been set (step 276). If the RAM FULL flag has not been set, the system determines whether the event/external connect flag has been set (step 280). When the event/external connect flag has been set, the system determines whether an event or an external connection triggered the flag (step 284). If the event button triggered the flag, the information is updated in the event portion of the internal RAM (step 286). If an external connection triggered the flag, the external interface routine is run (step 288). Upon completion of the external interface routine, the system exits to the power up initialization sequence (step 290).

If the event/external connect flag is not set (see step 280), or when the event information has been updated in the event buffer (step 280), the system determines whether it is time to update the display (step 182). If it is not time to update the display, the system returns to the power-down mode (step 268). If it is time to update the display, the system reads and displays the updated time of day (step 264).

Figure 13C:
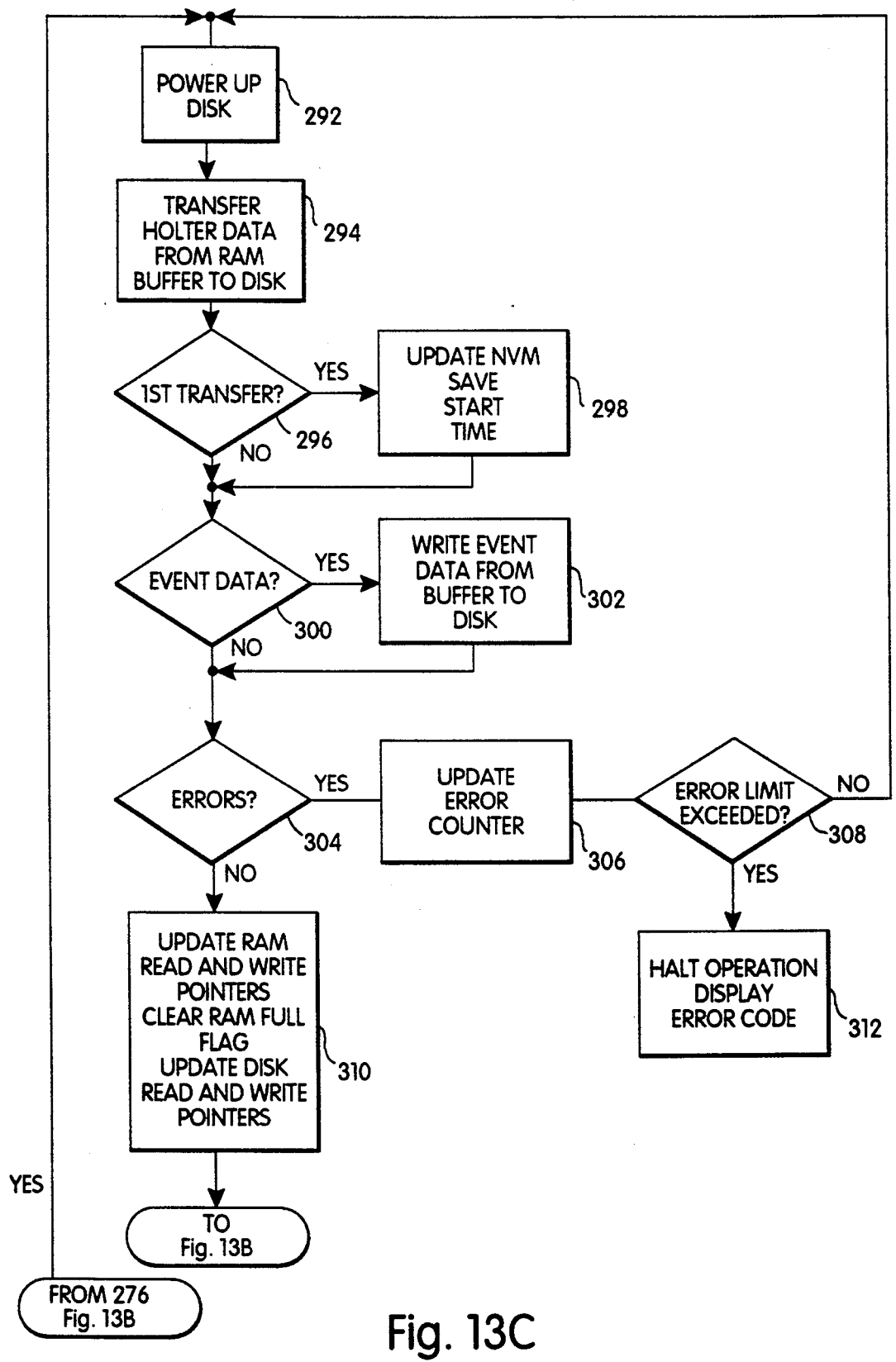

If the RAM FULL flag has been set (step 276), the steps shown in FIG. 13C are performed. The disk drive is powered-up (step 292), and ECG data then is transferred from the data buffer to the disk drive (step 294). The system determines whether the transfer is the first data transfer (step 296). In the case of a first transfer, the non-volatile memory of the clock is updated to reflect the time of the first transfer. The system also determines whether there is an event data held in the RAM (step 300). If event data is present, the event data is written from the RAM buffer to the disk (step 302).

During the transfer, the system determines whether any errors have occurred (step 304). If an error does occur, the system updates the error counter (step 306).

When the error limit is exceeded (step 308), monitor operation is halted and an error code is displayed (step 312). Upon completion of the data transfer, the read and write pointers for the RAMs are updated and the RAM FULL flag is cleared (step 310). Moreover, the read and write pointers for the disks are updated. The system then returns to check the event/external connect flag (step 280, FIG. 13B).

Figure 13D:
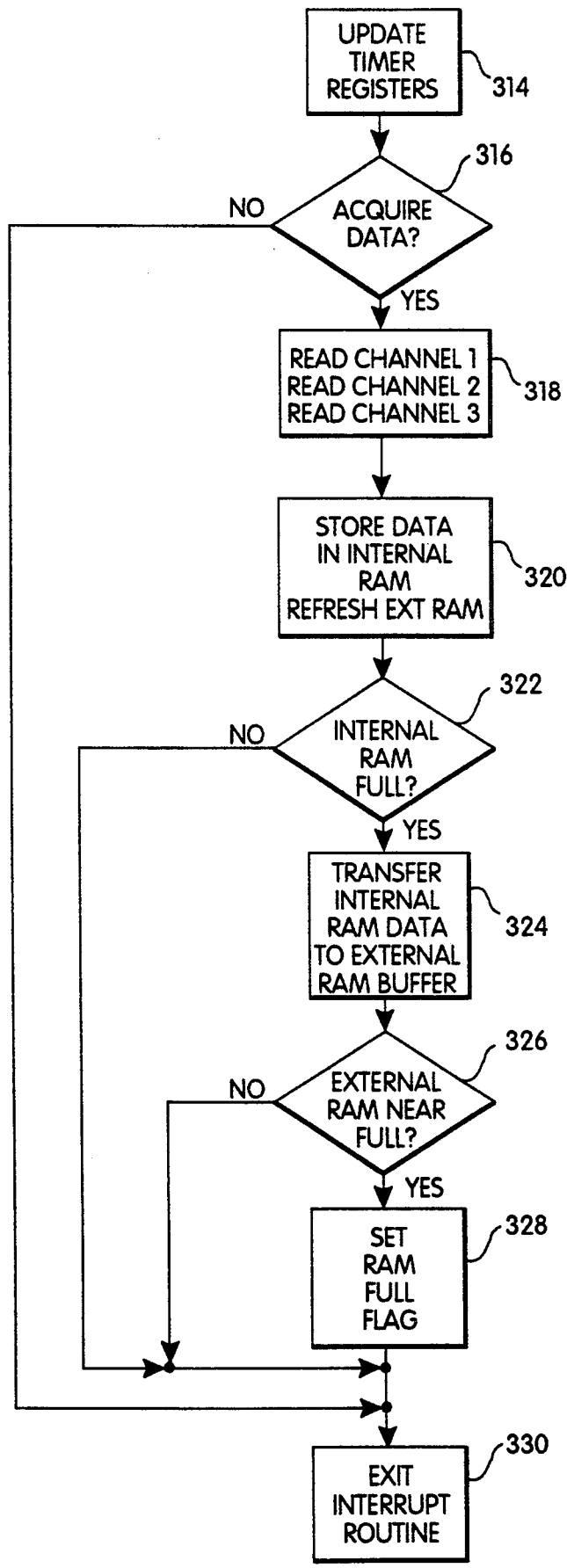
FIG. 13D is a flow chart depicting the steps performed by the CPU of FIG. 7 when running an interrupt routine in high resolution mode.

FIG. 13D depicts the steps of the interrupt routine which is called in step 248 of FIG. 13A. Like the interrupt routine for the Holter mode, this routine runs in the foreground while the routine of FIGS. 13A–13C runs in the background. Initially in this routine, the timer registers are updated (step 314). The system then determines whether it is in a data acquisition mode (step 316). If the system is not in a data acquisition mode, it exits the interrupt routine (step 330). If the system is in a data acquisition mode, it reads the three channels of digitized ECG data (step 318, FIG. 13D) from the ADC buffers of the amplifier 46 (see FIG. 5). In this instance, the system does not determine whether the third channel is enabled because in the high resolution mode, all three channels are utilized. Then the system stores the data in the internal RAM of the controller and refreshes the external RAM of the data buffer (step 320).

If the internal RAM is full, the data in the internal RAM is transferred to one of the external RAMs of the data buffer (step 324). After such a transfer, the system determines whether the external RAM is near full (step 326). If the external RAM is near full, the RAM FULL flag is set (step 328). If the internal RAM is not full, as checked in step 322 or if the external RAM is not near full, as checked in step 326, or if the RAM full flag has been set, as in step 328, the system exits the interrupt routine (step 330).

Figure 14:
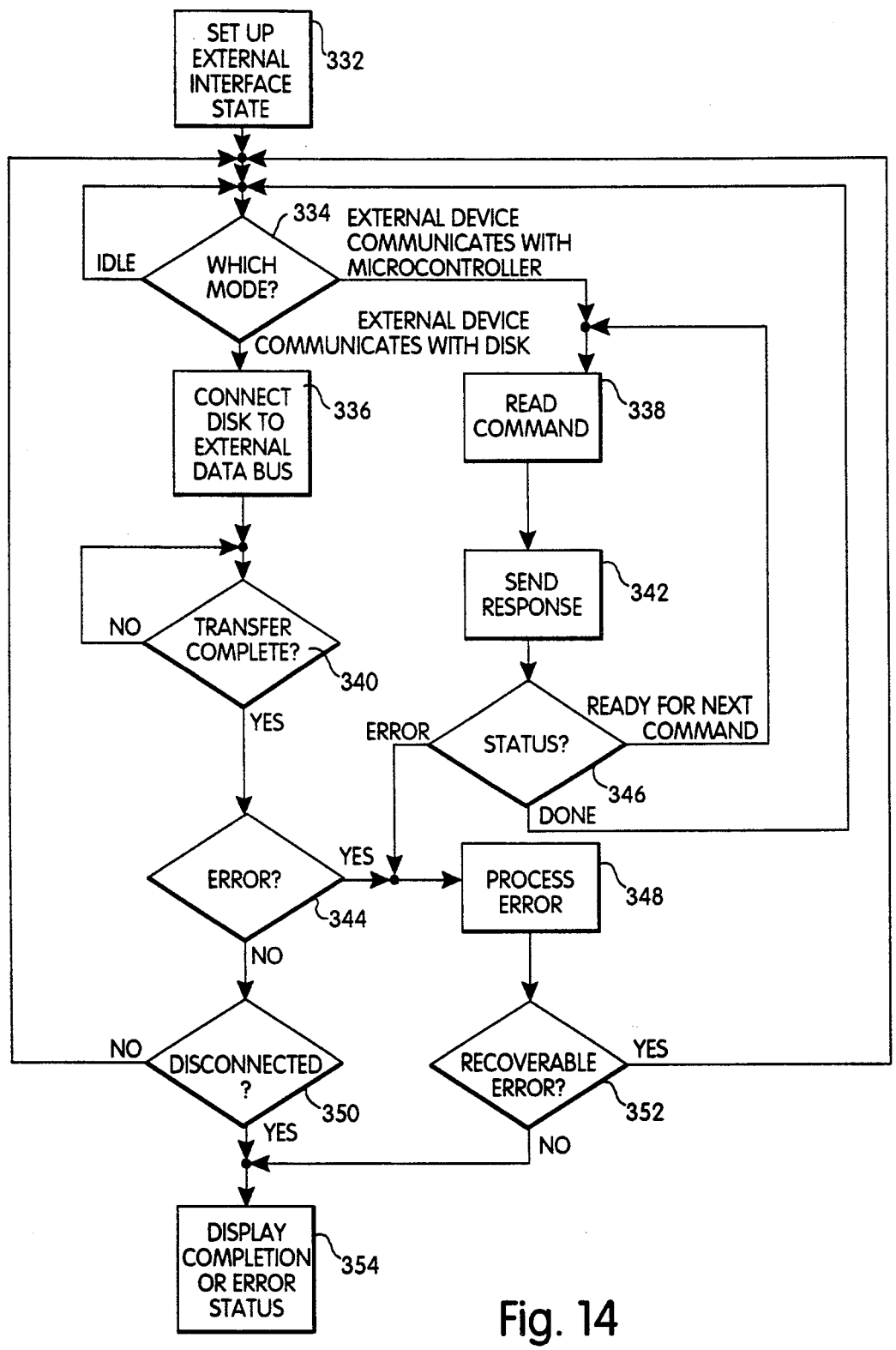
FIG. 14 is a flow chart depicting the steps performed by the CPU of FIG. 7 when running the external connect routine.

FIG. 14 is a flow chart showing the steps of the external interface routine. Initially, the system sets up the external interface state (step 332). The system subsequently determines its current mode of operation (step 334). If the system is in an idle mode, it continues to loop and determines its operating mode. The system may also operate in a mode where the external device communicates directly with the disk drive. When operating in such a mode, the system connects the disk drive to the external data bus (step 336). As mentioned previously, the external data bus is exclusively dedicated for access by an external data processing system. The system waits until the transfer has been completed (see step 340). If an error occurred during the transfer (see step 344), the system processes the error (step 348). With such processing, the system determines whether the error is a recoverable error (step 352). If the error is a non-recoverable error, the system displays appropriate information indicating the error status (step 354). However, if the error is recoverable, the system continues in the external mode.

If no error occurs during the transfer of the data to the external device, the system waits until it is disconnected. Upon being disconnected, it displays the completion status on the display (step 354). The system may also operate in a mode where the external device communicates with the controller 48 (FIG. 4). When operating in this mode, the controller 48 reads a command (step 338) and sends a response (step 342). The CPU then checks the status of the system. If an error occurred, the system processes the error (step 348). If the CPU is done communicating with the external device, it, again, returns to step 334, wherein it checks the current mode of operation. Lastly, if the system is ready to accept a new command, it reads the next command (step 338) and again sends a response (step 342).

While the invention has been shown with reference to a preferred embodiment thereof, it will be understood by those skilled in the art that changes in form and detail may be made without departing from the spirit and scope of the present invention as defined herein in the appended claims. For instance, the present invention is not limited to ECG data. The monitor unit may also be used to record other types of physiological data such as blood pressure.

I claim:

1. A method for ambulatory recording of physiological data from a patient, said physiological data being used for subsequent medical diagnosis, comprising the steps of:
   attaching an ambulatory physiological monitor containing a high capacity, miniaturized magnetic disk storage unit to an ambulatory patient;
   obtaining physiological data from the patient while the patient is ambulatory using said ambulatory physiological monitor;
   storing the physiological data in said disk storage unit while the patient is ambulatory; and
   detaching said ambulatory physiological monitor from the ambulatory patient and transferring said physiological data from said disk storage unit to an external system for analysis and medical diagnosis.

2. An ambulatory physiological monitor for recording physiological data from a patient for subsequent medical diagnosis of the patient, comprising:
   transducer means for attachment to an ambulatory patient for sensing at least one physiological parameter of the ambulatory patient and providing a physiological signal representative of the physiological parameter;
   storage means for storing physiological data, said storage means comprising a high capacity, miniaturized magnetic disk storage unit;
   circuit means for converting said physiological signal to physiological data, for transferring said physiological data to said disk storage unit, and for transferring said physiological data from said disk storage unit to an external system for subsequent analysis and medical diagnosis;
   a housing containing said disk storage unit and said circuit means; and
   means for attaching said housing to the ambulatory patient so that the patient is ambulatory during sensing and storage of physiological data.

3. An ambulatory physiological monitor as defined in claim 2 wherein said circuit means includes a buffer memory for temporary storage of said physiological data, means for transferring said physiological data from said buffer memory to said disk storage unit during spaced apart intervals, and means for energizing said disk storage unit only during said spaced apart intervals.

4. An ambulatory physiological monitor as defined in claim 3 wherein said buffer memory includes means for acquiring physiological data without interruption as physiological data is transferred from said buffer memory to said disk storage unit.

5. An ambulatory physiological monitor as defined in claim 2 wherein said circuit means includes means for sampling said physiological signal at a sampling rate of at least 200 samples per second to provide said physiological data and wherein said disk storage unit has sufficient capacity to record at east 24 hours of continuous, uncompressed physiological data.

6. An ambulatory physiological monitor as defined in claim 2 wherein said circuit means includes means for sampling said physiological signal at a first rate in a high resolution mode to provide high resolution physiological data, means for sampling said physiological signal at a second rate that is lower than said first rate in a low resolution mode to provide low resolution physiological data and means for selecting said high resolution mode or said low resolution mode.

7. An ambulatory physiological monitor as defined in claim 6 wherein said first rate is greater than 800 samples per second and said second rate is at least 200 samples per second.

8. An ambulatory physiological monitor as defined in claim 6 further including an event button that can be activated by the patient and wherein said means for selecting said high resolution mode or said low resolution mode includes means for selecting said high resolution mode in response to activation of said event button.

9. An ambulatory physiological monitor as defined in claim 6 wherein said means for selecting said high resolution mode or said low resolution mode includes means for automatically selecting said high resolution mode at predetermined intervals.

10. An ambulatory electrocardiography monitor for recording electrocardiography data from a patient, comprising:
    a plurality of electrocardiography electrodes for attachment to an ambulatory patient for providing electrocardiography signals;
    storage means for storing electrocardiography data, said storage means comprising a high capacity, miniaturized magnetic disk storage unit;
    circuit means for converting said electrocardiography signals to electrocardiography data, for transferring said electrocardiography data to said disk storage unit, and for transferring said electrocardiography data from said disk storage unit to an external system for subsequent analysis and medical diagnosis;
    a housing containing said disk storage unit and said circuit means; and
    means for attaching said housing to said ambulatory patient so that the patient is ambulatory during sensing and storage of electrocardiography data.

11. An ambulatory electrocardiography monitor as defined in claim 10 wherein said circuit means includes a buffer memory for temporary storage of said electrocardiography data, means for transferring said electrocardiography data from said buffer memory to said disk storage unit during spaced apart intervals, and means for energizing said disk storage unit only during said spaced apart intervals.

12. An ambulatory electrocardiography monitor as defined in claim 10 wherein said circuit means includes means for sampling said electrocardiography signals at a sampling rate of at least 200 samples per second to provide said electrocardiography data and wherein said disk storage unit has sufficient capacity to record at least 24 hours of continuous, uncompressed electrocardiography data.

13. An ambulatory electrocardiography monitor as defined in claim 10 wherein said circuit means includes means for detecting pacemaker pulses in said electrocardiography signals, and means for separately storing the times of said pacemaker pulses on said disk storage unit.

14. An ambulatory electrocardiography monitor as defined in claim 13 further including an event button that can be activated by the patient and wherein said circuit means further includes means for recording the time of activation of said event button on said disk storage unit.

15. An ambulatory electrocardiography monitor as defined in claim 10 wherein said circuit means includes means for sampling said electrocardiography signals at a first rate in a high resolution mode to provide high resolution electrocardiography data means for sampling said electrocardiography signals at a second rate that is lower than said first rate in a low resolution mode to provide low resolution electrocardiography data and means for selecting said high resolution mode or said low resolution mode.

16. An ambulatory electrocardiography monitor as defined in claim 10 further including a self-contained power supply for powering said monitor.

17. A method for recording physiological data from an ambulatory patient for subsequent medical diagnosis of the patient, comprising the steps of:
    attaching a transducer to an ambulatory patient;
    sensing at least one physiological parameter of the ambulatory patient with the transducer and providing a physiological signal representative of the physiological parameter;
    attaching to the ambulatory patient a housing containing a high capacity, miniaturized magnetic disk storage unit and a circuit, said circuit performing the steps of converting said physiological signal to physiological data and storing said physiological data in said disk storage unit, said housing being worn by the ambulatory patient during sensing and storage of physiological data; and
    subsequently detaching said housing from the ambulatory patient and transferring said physiological data from said disk storage unit to an external system for analysis and medical diagnosis.

18. A method as defined in claim 17 wherein the step of storing said physiological data includes the steps of temporarily storing said physiological data in a buffer memory, transferring said physiological data from said buffer memory to said disk storage unit during spaced apart intervals, and energizing said disk storage unit only during said spaced apart intervals.

19. An ambulatory electrocardiography monitor for recording electrocardiography data from a patient, comprising:
    a plurality of electrocardiography electrodes for attachment to an ambulatory patient for providing electrocardiography signals;
    storage means for storing electrocardiography data;
    circuit means for converting said electrocardiography signals to electrocardiography data, for transferring said electrocardiography data to said storage means, and for transferring said electrocardiography data from said storage means to an external system for subsequent analysis and medical diagnosis, said circuit means including means for sampling said electrocardiography signals at a first rate in a high resolution mode to provide high resolution electrocardiography data, means for sampling said electrocardiography signals at a second rate that is lower than said first rate in a low resolution mode to provide low resolution electrocardiography data and means for selecting said high resolution mode or said low resolution mode;
    a housing containing said storage means and said circuit means; and
    means for attaching said housing to the ambulatory patient so that the patient is ambulatory during sensing and storage of electrocardiography data.

20. An ambulatory electrocardiography monitor as defined in claim 19 wherein said storage means comprises a high capacity, miniaturized magnetic disk storage unit.

21. An ambulatory electrocardiography monitor as defined in claim 19 wherein said first rate is greater than 800 samples per second and said second rate is at least 200 samples per second.

22. An ambulatory electrocardiography monitor as defined in claim 21 further including an event button that can be activated by the patient and wherein said means for selecting said high resolution mode or said low resolution mode includes means for selecting said high resolution mode in response to activation of said event button.

23. An ambulatory electrocardiography monitor as defined in claim 21 wherein said means for selecting said high resolution mode or said low resolution mode includes means for automatically selecting said high resolution mode at predetermined intervals.

* * * * *